United States Patent [19]

Smith et al.

[11] Patent Number: 6,088,176

[45] Date of Patent: *Jul. 11, 2000

[54] METHOD AND APPARATUS FOR SEPARATING MAGNETIC AND THERMAL COMPONENTS FROM AN MR READ SIGNAL

[75] Inventors: Gordon J. Smith; Hal Hjalmar Ottesen, both of Rochester, Minn.; David William Abraham, Ossining; Anthony Paul Praino, Poughquag, both of N.Y.; Mark Edward Re, Los Gatos, Calif.; Hemantha Kumar Wickramasinghe, Chappaqua, N.Y.

[73] Assignee: International Business Machines Corporation, Armonk, N.Y.

[*] Notice: This patent is subject to a terminal disclaimer.

[21] Appl. No.: 08/581,877

[22] Filed: Jan. 2, 1996

Related U.S. Application Data

[63] Continuation-in-part of application No. 08/056,164, Apr. 30, 1993, Pat. No. 5,527,110.

[51] Int. Cl.$^7$ ....................................................... G11B 5/09
[52] U.S. Cl. ............................... 360/46; 360/75; 360/25; 360/31
[58] Field of Search .................................. 360/113, 77.06, 360/77.01, 103, 67, 75, 137, 46, 48, 32, 66, 77.05, 77.04, 59, 25, 31; 324/210, 212, 252, 207.21, 235; 374/4, 6, 9; 164/141, 45; 369/58, 116, 275.1; 388/812; 395/442; 73/866.4, 104; 361/111; 327/311; 364/724.16

[56] References Cited

U.S. PATENT DOCUMENTS

| | | |
|---|---|---|
| 3,416,373 | 12/1968 | Havens . |
| 3,918,091 | 11/1975 | Walraven et al. ............... 360/77.06 |
| 4,430,010 | 2/1984 | Zrenner et al. .................. 374/45 |
| 4,485,337 | 11/1984 | Sandusky ........................ 388/812 |
| 4,498,146 | 2/1985 | Martinez ......................... 395/442 |
| 4,532,802 | 8/1985 | Yeack-Scranton et al. ......... 73/866.4 |

(List continued on next page.)

FOREIGN PATENT DOCUMENTS

| | | |
|---|---|---|
| 0 242 597 | 10/1987 | European Pat. Off. . |
| 61-177622 | 8/1986 | Japan . |

(List continued on next page.)

OTHER PUBLICATIONS

S. Z. Dushkes and R. J. Surty, "Head Crash Detector", May 1971, IBM Technical Disclosure Bulletin, vol. 13, No. 12, p. 3685.

(List continued on next page.)

*Primary Examiner*—Alan T. Faber
*Attorney, Agent, or Firm*—Mark A. Hollingsworth

[57] ABSTRACT

An apparatus and method for reading an information signal from a magnetic storage medium using a magnetoresistive (MR) head, and separating a thermal signal component and, if present, a magnetic signal component from the information signal. A signal separation/restoration module eliminates distortion in the magnetic signal component of a readback signal induced by a thermal signal component of the readback signal. A finite impulse response (FIR) filter may be employed in the signal separation/restoration module to eliminate the distortion in the magnetic signal. The signal separation/restoration module may be employed to extract the thermal signal component from the readback signal. In one configuration, an MR head is coupled to an arm electronics (AE) module, having a highpass filtering behavior, and a signal separation/restoration module that includes an inverse filter having a transfer function inverse to that of the effective highpass filter of the AE module. The inverse filter may be an infinite impulse response (IIR) filter. In another embodiment, the magnetic and thermal signal components of a readback signal are respectively extracted and processed so as to linearly correspond to head-to-disk spacing. Head-to-disk spacing change using the thermal signal is used to detect disk surface defects, topographic variations, and servo control surface variations.

77 Claims, 31 Drawing Sheets

U.S. PATENT DOCUMENTS

| | | | |
|---|---|---|---|
| 4,647,992 | 3/1987 | Vinal | 360/77.01 |
| 4,669,011 | 5/1987 | Lemke | 360/103 |
| 4,691,259 | 9/1987 | Imakoshi et al. | 360/113 |
| 4,712,144 | 12/1987 | Klaassen | 360/67 |
| 4,747,698 | 5/1988 | Wickramsinghe et al. | 374/6 |
| 4,762,427 | 8/1988 | Hori et al. | 374/141 |
| 4,777,544 | 10/1988 | Brown et al. | 360/75 |
| 4,802,033 | 1/1989 | Chi | 360/77.04 |
| 4,853,810 | 8/1989 | Pohl et al. | 360/103 |
| 4,914,398 | 4/1990 | Jove et al. | 361/111 |
| 4,931,887 | 6/1990 | Hegde et al. | 360/75 |
| 4,949,036 | 8/1990 | Bezinque et al. | 324/212 |
| 5,032,935 | 7/1991 | Jove et al. | 360/67 |
| 5,054,936 | 10/1991 | Fraden | 374/164 |
| 5,057,785 | 10/1991 | Chung et al. | 327/311 |
| 5,070,495 | 12/1991 | Bletscher, Jr. et al. | 369/116 |
| 5,079,663 | 1/1992 | Ju et al. | 360/113 |
| 5,084,791 | 1/1992 | Thanos et al. | 360/77.04 |
| 5,130,866 | 7/1992 | Klaassen et al. | 360/75 |
| 5,168,413 | 12/1992 | Coker et al. | 360/137 |
| 5,185,681 | 2/1993 | Volz et al. | 360/77.05 |
| 5,212,677 | 5/1993 | Shimote et al. | 369/58 |
| 5,233,482 | 8/1993 | Galbraith et al. | 360/46 |
| 5,258,940 | 11/1993 | Coker et al. | 364/724.16 |
| 5,301,080 | 4/1994 | Ottesen et al. | 360/113 |
| 5,321,559 | 6/1994 | Nguyen et al. | 360/46 |
| 5,327,298 | 7/1994 | Ottesen et al. | 360/48 |
| 5,345,342 | 9/1994 | Abbott et al. | 360/48 |
| 5,367,409 | 11/1994 | Ottesen et al. | 360/32 |
| 5,377,058 | 12/1994 | Good et al. | 360/75 |
| 5,388,014 | 2/1995 | Brug et al. | 360/66 |
| 5,402,278 | 3/1995 | Morita | 360/77.05 |
| 5,418,770 | 5/1995 | Ide et al. | 369/116 |
| 5,424,885 | 6/1995 | McKenzie et al. | 360/77.05 |
| 5,430,706 | 7/1995 | Utsunomiya et al. | 369/275.1 |
| 5,455,730 | 10/1995 | Dovek et al. | 360/113 |
| 5,739,972 | 4/1998 | Smith et al. | 360/77.03 |
| 5,751,510 | 5/1998 | Smith et al. | 360/77.03 X |

FOREIGN PATENT DOCUMENTS

| | | |
|---|---|---|
| 63-191316 | 8/1988 | Japan . |
| 1-98180 | 4/1989 | Japan . |
| 4-95218 | 3/1992 | Japan . |
| 4-109421 | 4/1992 | Japan . |
| 4-141822 | 5/1992 | Japan . |
| 5-174515 | 7/1993 | Japan . |
| 06290563 | 10/1994 | Japan . |

OTHER PUBLICATIONS

L. R. Bellamy and J. D. Luciani, "Disk Drive Motor Speed Control", Apr. 1981, IBM Technical Disclosure Bulletin, vol. 23, No. 11, p. 5163.

E. G. Gruss and A. R. Tietze, "Servo System for Magnetic Recording Based on Time Comparison", Jul. 1980, IBM Technical Disclosure Bulletin vol. 23, No. 2, pp. 787–789.

R. E. Fontana, Jr., D. E. Horne and H. Sussner, "Disk Asperity Detector", Aug. 1983, IBM Technical Disclosure Bulletin, vol. 26, No. 3A, pp. 1278–1280.

G. J. Kerwin, J. M. Poss and D. P. Swart, "Fast Offset Recovery for Thermal Asperity Data Recovery Procedure", Apr. 1992, IBM Technical Disclosure Bulletin, vol. 34, No. 11, pp. 217–219.

K. B. Klaassen, "Magnetic Recording Channel Front–Ends", Nov. 1, 1991, IBM Research Report, pp. 1–6.

Research Disclosure, "Asperity Knee Detection Using Harmonic Ratio Flyheight", Mar. 1991, Emsworth Design, Inc., No. 323, p. 190.

Chau Lin, "Techniques for the Measurement of Air–Bearing Separation–A Review", Dec. 1973, IEEE Transactions on Magnetics, vol. MAG–9, No. 4, pp. 673–677.

F. W. Gorter et al., "Magnetoresistive Reading of Information", Sep. 1974, IEEE Transactions on Magentics, vol. MAG–10, No. 3, pp. 899–902.

F. E. Talke et al., "Surface Defect Studies of Flexible Media Using Magnetoresistive Sensors", Sep. 1975, IEEE Transactions on Magnetics, vol. MAG–11, No. 5, pp. 1188–1190.

Shoji Tanaka, et al., "Characterization of Magentizing Process for Pre–Embossed Servo Pattern of Plastic Hard Disks", Mar. 1994, IEEE Transactions on Magnetics, vol. 30, No. 2, pp. 4210–4211.

Hiroaki Yada et al., "High Areal Density Recording Using an MR/Inductive Head and Pre–Embossed Rigid Magnetic Disk", Mar. 1994, IEEE Transactions on Magentics, vol. 30, No. 2, pp. 404–409.

Y. Li et al., "The Determination of Flash Temperature in Intermittent Magentic Head/Disk Contacts Using Magnetoresistive Heads", Jan. 1993, Journal of Tribology, vol. 115, No. 1, pp. 179–184.

Shoji Tanaka et al., "Characterization of Magnetizing Process for Pre–Embossed Servo Pattern of Plastic Hard Disks", Nov. 1994, IEEE Transactions on Magnetics, vol. 30, No. 6, pp. 4209–4211.

Kenjiro Watanabe et al., "Demonstration of Track Following Technique Based on Discrete Track Media", Nov. 1993, IEEE Transactions on Magnetics, vol. 29, No. 6, pp. 4030–4032.

K. Watanabe et al., Demonstration of Track following Technic Based on Discrete Track Media, pp. 1–3.

Osamu Morita et al., "Magnetizatin Characteristics of Pre–Embossed Patterns on the Molded Plastic Rigid Disk."

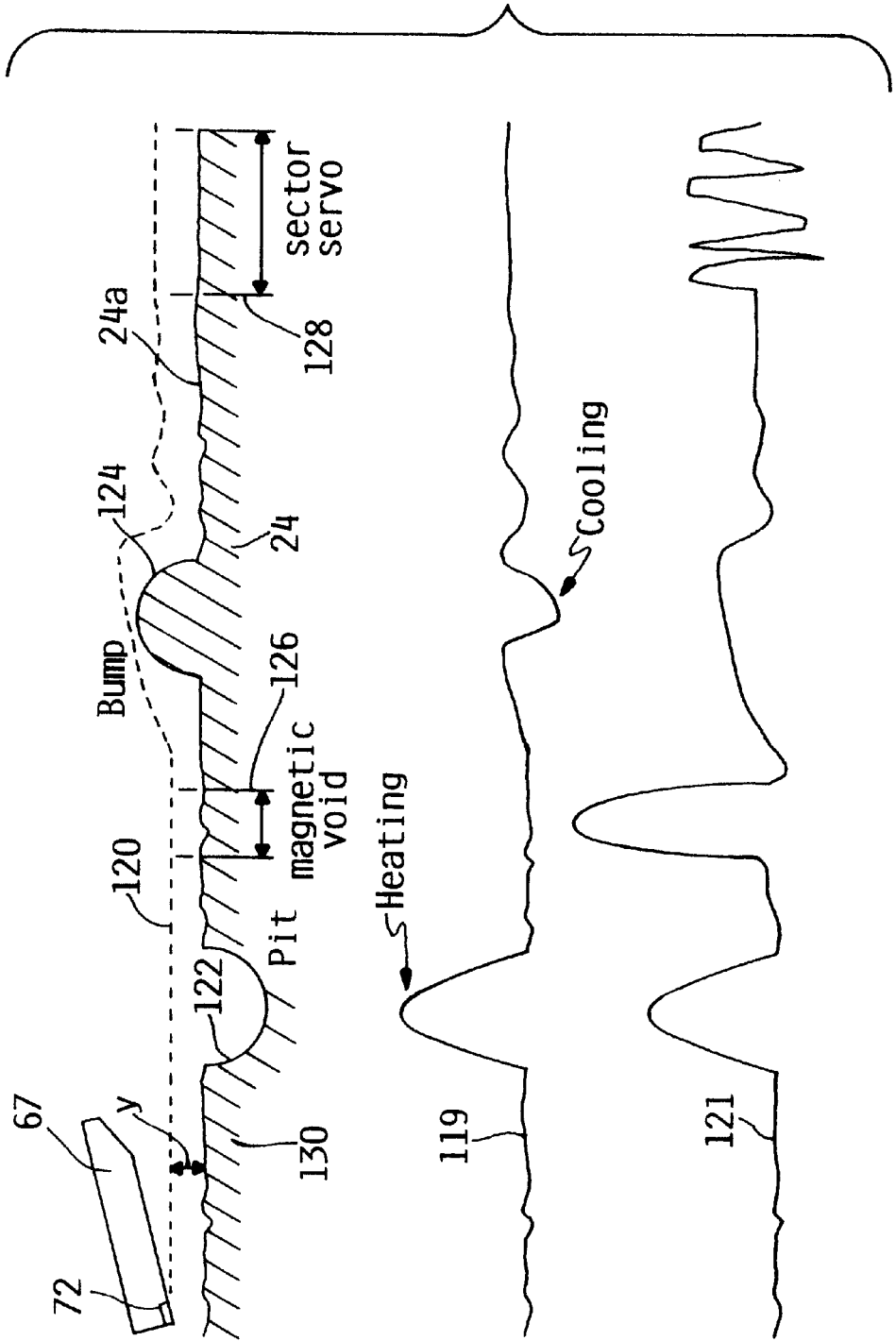

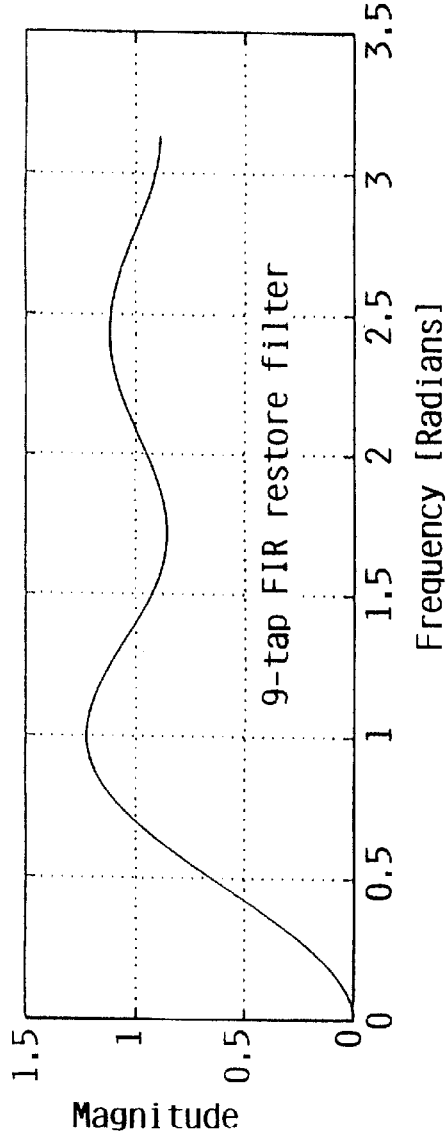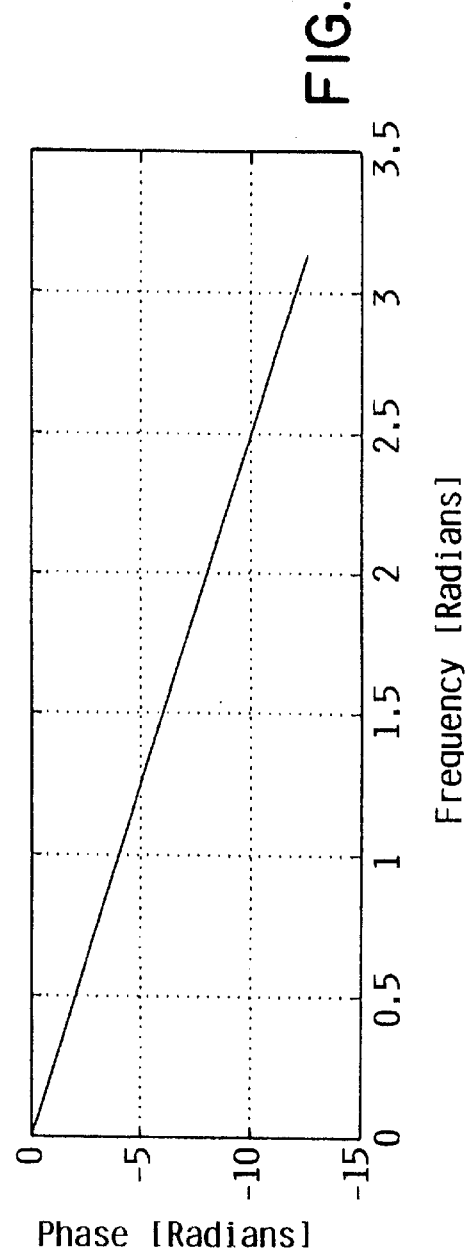

METHOD AND APPARATUS FOR SEPARATING MAGNETIC AND THERMAL COMPONENTS FROM AN MR READ SIGNAL

RELATED APPLICATION

This application is a continuation-in-part of application U.S. Ser. No. 08/056,164 filed on Apr. 30, 1993 now U.S. Pat. No. 5,527,110.

FIELD OF THE INVENTION

The present invention relates generally to data storage systems and, more particularly, to a method and apparatus for using a thermal component of a signal induced in a magnetoresistive (MR) head.

BACKGROUND OF THE INVENTION

A typical data storage system includes a magnetic medium for storing data in magnetic form and a transducer used to write and read magnetic data respectively to and from the medium. A disk storage device, for example, includes one or more data storage disks coaxially mounted on a hub of a spindle motor. The spindle motor rotates the disks at speeds typically on the order of several thousand revolutions-per-minute. Digital information is typically stored in the form of magnetic transitions on a series of concentric, spaced tracks comprising the surface of the magnetizable rigid data storage disks. The tracks are generally divided into a plurality of sectors, with each sector comprising a number of information fields, including fields for storing data, and sector identification and synchronization information, for example.

The actuator assembly typically includes a plurality of outwardly extending arms with one or more transducers and slider bodies being mounted on flexible suspensions. A slider body is typically designed as an aerodynamic lifting body that lifts the transducer head off of the surface of the disk as the rate of spindle motor rotation increases, and causes the head to hover above the disk on an air-bearing produced by high speed disk rotation. The distance between the head and the disk surface, typically on the order of 50–100 nanometers (nm) is commonly referred to as head-to-disk spacing.

Writing data to a data storage disk generally involves passing a current through the write element of the transducer assembly to produce magnetic lines of flux which magnetize a specific location of the disk surface. Reading data from a specified disk location is typically accomplished by a read element of the transducer assembly sensing the magnetic field or flux lines emanating from the magnetized locations of the disk. As the read element passes over the rotating disk surface, the interaction between the read element and the magnetized locations on the disk surface results in the production of electrical signals, commonly referred to as readback signals, in the read element.

Conventional data storage systems generally employ a closed-loop servo control system for positioning the read/write transducers to specified storage locations on the data storage disk. During normal data storage system operation, a servo transducer, generally mounted proximate the read/write transducers, or, alternatively, incorporated as the read element of the transducer, is typically employed to read information for the purpose of following a specified track (track following) and locating (seeking) specified track and data sector locations on the disk.

In accordance with one known servo technique, embedded servo pattern information is written to the disk along segments extending in a direction generally outward from the center of the disk. The embedded servo patterns are thus formed between the data storing sectors of each track. It is noted that a servo sector typically contains a pattern of data, often termed a servo burst pattern, used to maintain optimum alignment of the read/write transducers over the centerline of a track when reading and writing data to specified data sectors on the track. The servo information may also include sector and track identification codes which are used to identify the location of the transducer.

Within the data storage system manufacturing industry, much attention is presently being focused on the use of an MR element as a read transducer. Although the MR head, typically incorporating an MR read element and a thin-film write element, would appear to provide a number of advantages over conventional thin-film heads and the like, it is known by those skilled in the art that the advantages offered by the MR head are not fully realizable due to the present inability of data storage systems to accommodate a number of undesirable MR head characteristics.

In particular, MR element transducers introduce a distortion in the sensed magnetic signal, which typically represents data or servo information stored on a magnetic storage disk. The distortion to the magnetic signal is caused by many factors, including a number of undesirable characteristics inherent in the MR element and the specific configuration and orientation of the MR element when incorporated into an MR transducer assembly. By way of example, it is known that a typical MR element exhibits variations in read sensitivity along the width of the MR element which has been identified as a contributing factor to servo control errors of varying severity. Depending on the magnitude of the magnetic signal distortion introduced by the MR element, servo sector information may, for example, be misinterpreted or unreadable, resulting in the possible interruption or loss of servo control or, in some cases, an irretrievable loss of the data stored on the disk.

A considerable amount of industry attention and resources have been, and continue to be, expended to develop solutions directed at reducing or eliminating the detrimental effects associated with a distorted magnetic readback signal. Such distortion in a readback signal obtained by an MR transducer has heretofore been treated collectively as undesirable noise without a full appreciation of the response of the MR element to varying influences encountered within its operating environment. As yet, no satisfactory solution has been found to eliminate or substantially reduce the magnetic signal distortion introduced by an MR element.

There exists a keenly felt need in the data storage system manufacturing community for an apparatus and method for eliminating the undesirable distortion to a magnetic readback signal induced in an MR element. There exists a further need to provide such apparatuses and methods which are suitable for incorporation into existing data storage systems, as well as into new system designs. The present invention is directed to these and other needs.

SUMMARY OF THE INVENTION

The present invention is an apparatus and method for reading an information signal from a magnetic storage medium using a magnetoresistive (MR) element, and separating a thermal signal component and, if present, a magnetic signal component from the information signal. The magnetic signal is processed to remove the influence of the thermal signal component from the magnetic signal. A signal separation/restoration module eliminates modulation of the magnetic signal component of a readback signal induced by a thermal signal component of the readback signal. A finite impulse response (FIR) filter may be employed in the signal separation/restoration module to eliminate the modulation in the magnetic signal. The signal separation/restoration module may also be employed to extract the thermal signal component from the readback signal.

In accordance with a disk drive embodiment in which an MR element is coupled to an arm electronics (AE) module having a highpass filtering behavior, a signal separation/restoration module may be configured to include an inverse filter having a transfer function inverse to that of the effective highpass filter of the AE module. An infinite impulse response (IIR) filter may be programmed to reverse the amplitude and phase distortion of a thermal signal introduced by the highpass filtering behavior of the AE module.

In accordance with another embodiment, the magnetic and thermal signal components of a readback signal are respectively extracted and processed so as to linearly correspond to head-to-disk spacing. Head-to-disk spacing using the thermal signal may be used to detect disk surface defects and topographic variations. The thermal signal may be calibrated using a magnetic spacing signal in order to directly measure head-to-disk spacing change. The thermal head-to-disk spacing signal may be utilized for other systemic and diagnostic purposes, including defect characterization, error correction, and predictive failure analysis.

In a further embodiment, servo control information may be provided on the disk surface in the form of topographical variations. A thermal servo signal is induced in the MR element as the head passes over the topographical variations, extracted, and communicated as signals to actuator and spindle servo controls. Changes in the emissivity and/or absorptivity of the disk surface material may also be sensed by the MR element and transduced to a corresponding thermal signal.

BRIEF DESCRIPTION OF THE DRAWINGS

FIG. 7 is an exaggerated side view showing a data storage disk exhibiting various surface defects and features, and a thermal response and magnetic spacing response of an MR element to such defects and features;

FIG. 12 illustrates the magnitude and phase response of a finite impulse response (FIR) filter used in a signal separation/restoration module;

DETAILED DESCRIPTION OF THE EMBODIMENTS

Figure 1:
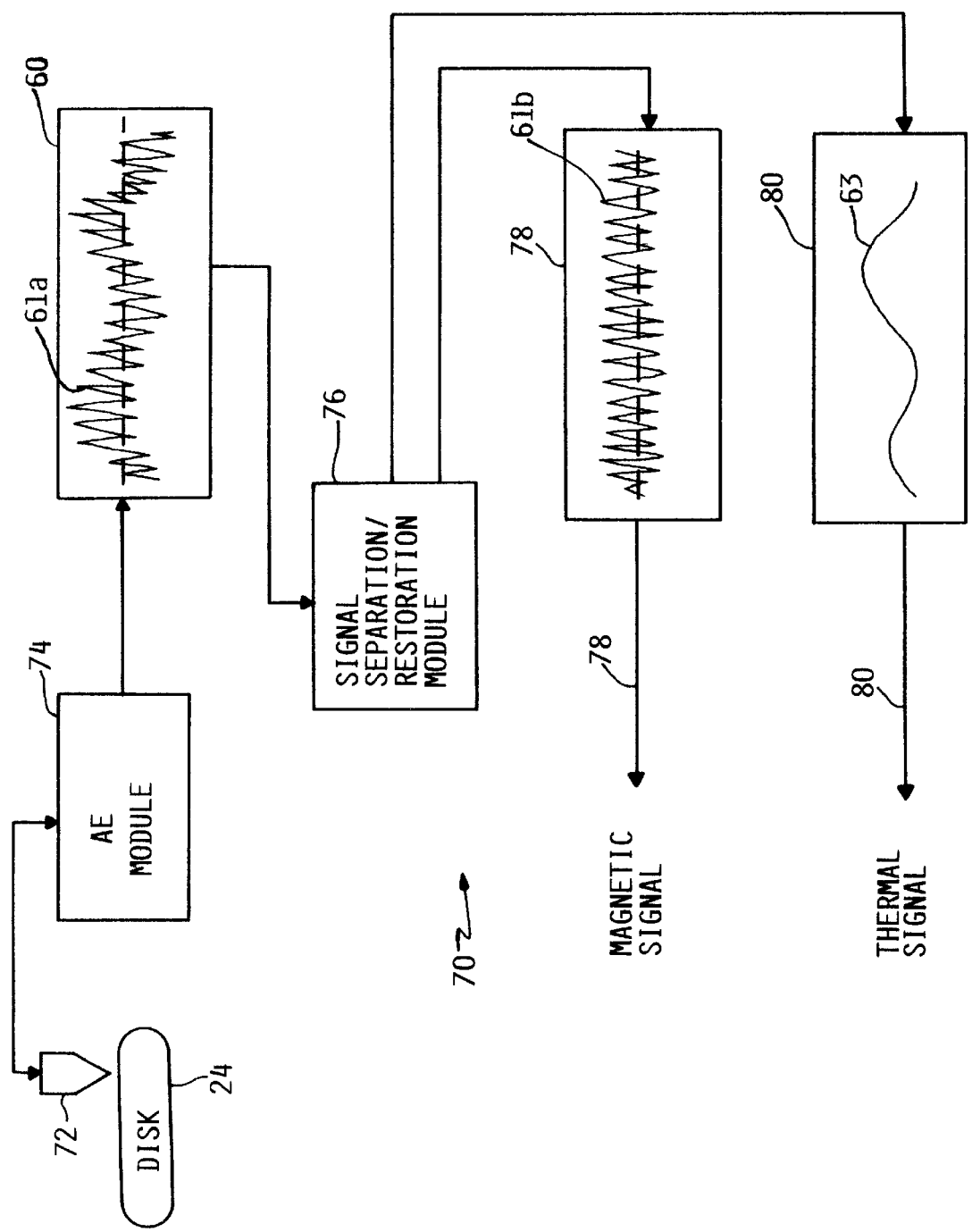
FIG. 1 is a block diagram of an apparatus for extracting a thermal signal and a magnetic signal from a readback signal induced in an MR head.

Referring now to the drawings and, more particularly, to FIG. 1, there is illustrated an apparatus 70 for reading an information signal having a magnetic signal component and a thermal signal component from a magnetic storage medium and for separating the thermal and magnetic signal components from the information signal. The magnetic signal is processed to remove the influence of the thermal signal component from the magnetic signal. The two independent magnetic and thermal signals may then be utilized to enhance the operation, performance, and reliability of the data storage system.

In FIG. 1, a magnetoresistive (MR) element 72 is shown in close proximity with a surface of a data storage disk 24. The information read by the MR element 72 from the disk 24 is generally referred to herein as a readback signal. The readback signal produced in the MR element 72 is typically amplified by the arm electronics (AE) module 74. Filtering of the readback signal by the AE module 74 may also be performed. As shown in graphical form at the output of the AE module 74, the analog readback signal 60, containing a relatively high frequency magnetic signal component 61a, exhibits a distorted D.C. baseline due to the presence of a low frequency modulating signal component. It is appreciated by those skilled in the art that a modulated readback signal 60, or more particularly, a modulated magnetic signal component 61a of the readback signal 60 has long been identified as one source of a number of data storage system maladies, including servo control errors and inaccuracies, causing a reduction in data storing and retrieving reliability, and, in some cases, an irretrievable loss of data.

As discussed previously in the Background of the Invention Section, a considerable amount of industry attention and resources have been expended to fully comprehend the nature and origins of the undesirable readback signal baseline modulation. As will be discussed in greater detail hereinbelow, it has been discovered by the inventors that the readback signal 60 is a composite signal comprising independent magnetic and thermal signal components, and that the low frequency modulation in the readback signal is, in actuality, an independent thermal information signal component of the readback signal 60. It has further been determined by the inventors, as will also be discussed in detail hereinbelow, that undesirable readback signal 60 modulation can be eliminated or substantially reduced in magnitude, thus providing for a virtually pure magnetic signal representative of data or servo information.

Importantly, the up-to-now bothersome thermal signal component of a readback signal, referred to generally herein as the thermal signal, also includes an informational content which may be extracted from the readback signal 60 and utilized for a variety of advantageous purposes heretofore unappreciated by those skilled in the art. The thermal signal 63, for example, may be employed by the servo control to provide for reliable track following and track seeking operations, in contrast to using the magnetic signal 61a typically used in accordance with a conventional servo control approach. It has further been determined that the thermal signal 63 contains information that can be used to determine the flyheight of an MR element 72 with respect to a disk surface 24 to an accuracy on the order of 1 nanometer, and can be utilized for a number of other purposes, including disk surface analysis and topographical mapping, disk defect detection and screening, error correction, and predictive failure analysis (PFA), for example.

Figure 2:
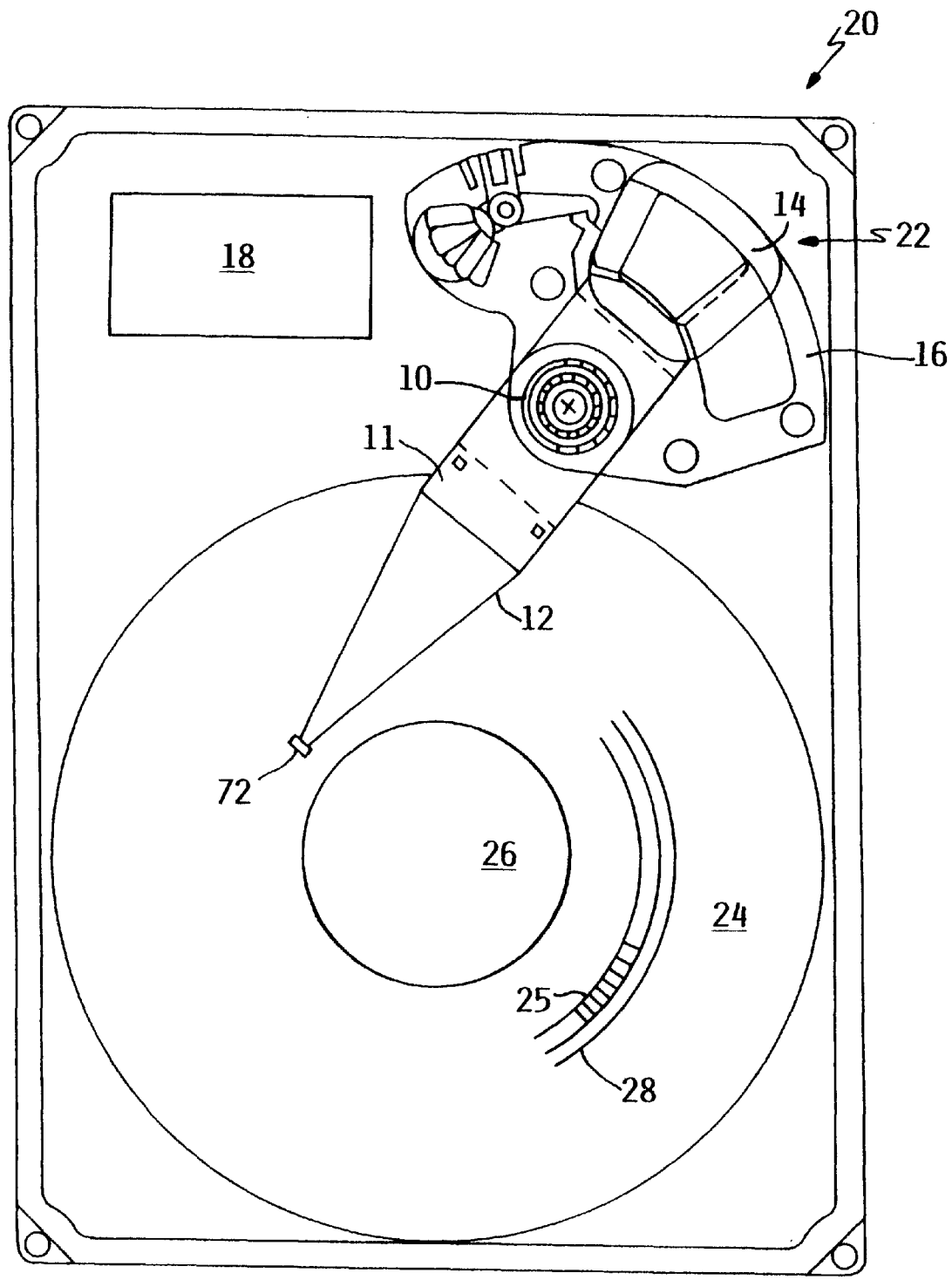
FIG. 2 is a top view of a data storage system with its upper housing cover removed.

The apparatus illustrated in FIG. 1 may be included as part of the design of a new generation of data storage systems which exploit the availability of a restored, non-modulated magnetic readback signal 61 and an independent thermal signal 63, and may also be incorporated into existing data storage systems using standard MR heads as part of a retrofit program. In general, and as illustrated in FIG. 2, a data storage system 20 employing MR transducers typically includes one or more rigid data storage disks 24 which rotate about a spindle motor 26. An actuator assembly 10 typically includes a plurality of interleaved actuator arms 11 and suspension 12, with each suspension supporting one or more MR head transducers 72 for reading and writing information to and from the data storage disks 24.

The actuator assembly 10 includes a coil assembly 14 which cooperates with a permanent magnet assembly 16 to operate as an actuator voice coil motor 22 responsive to control signals produced by a controller 18. The controller 18 coordinates the transfer of data to and from the data storage disks 24, and cooperates with the actuator voice coil motor 22 to move the actuator arms/suspensions 11/12 and MR transducers 72 to prescribed track 28 and sector 25 locations when reading and writing data to and from the disks 24.

Figure 3A:
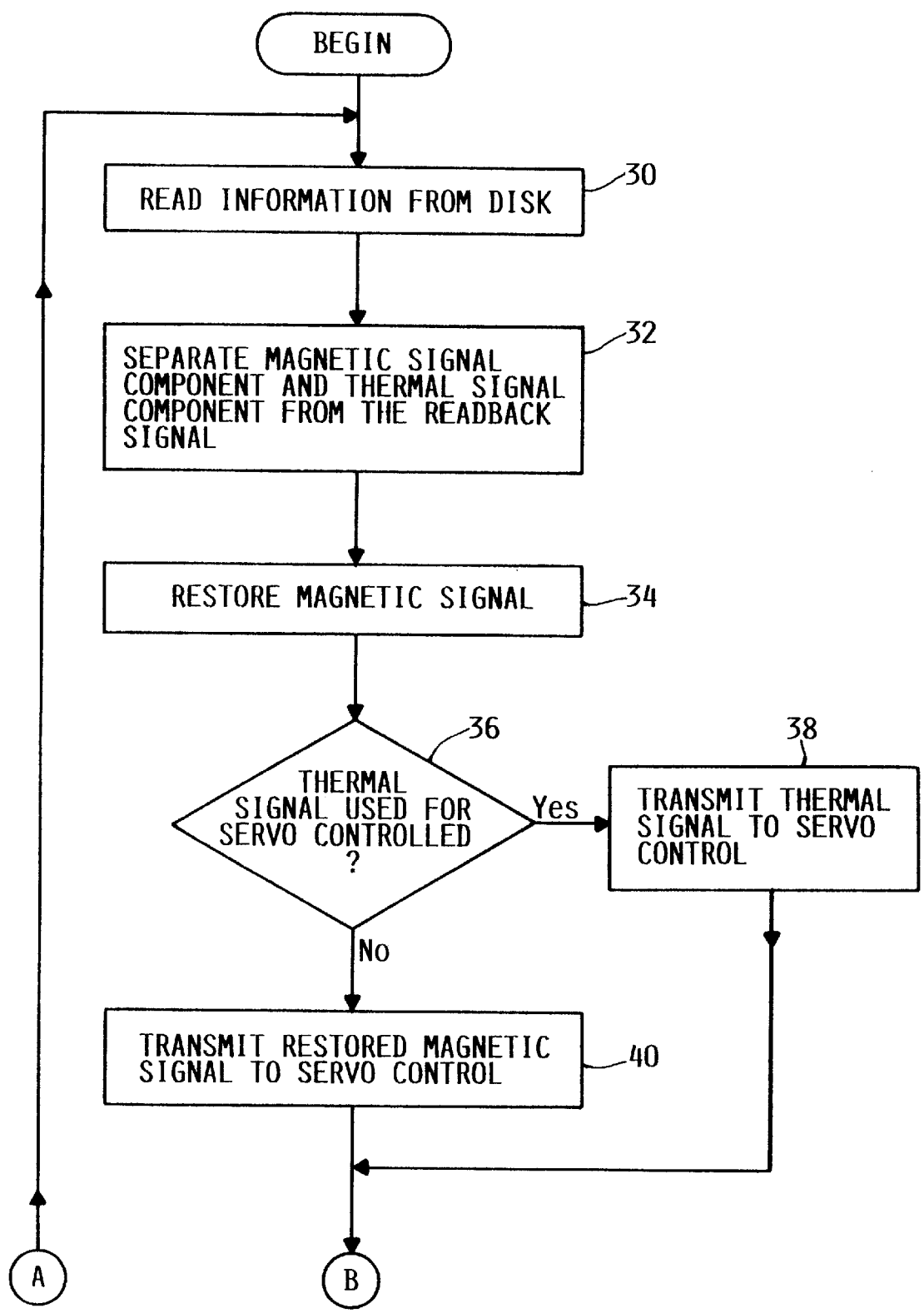
FIG. 3 is a flow diagram illustrating a method for obtaining and utilizing a thermal signal component of a readback signal.
Figure 3B:
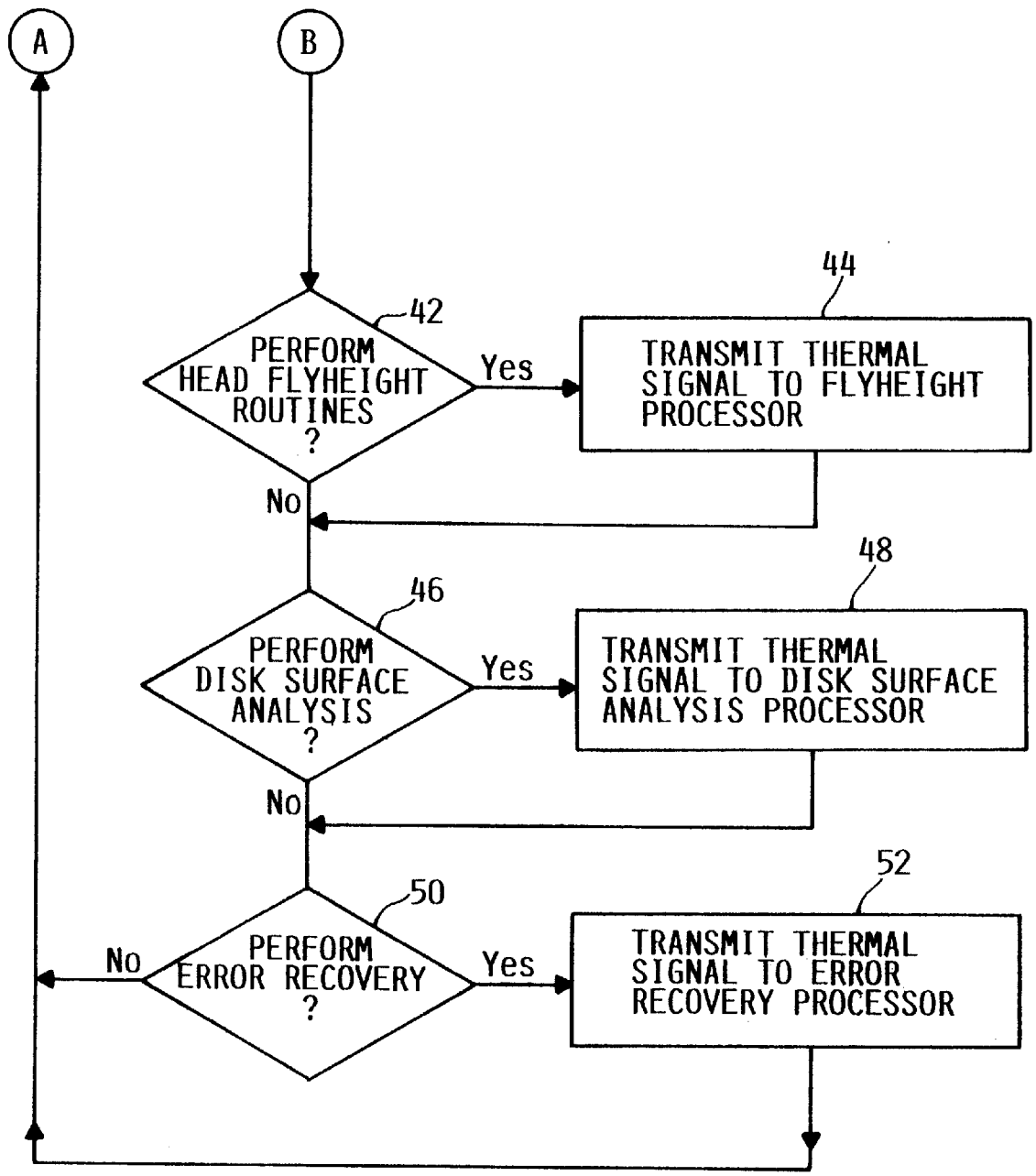

For purposes of providing an understanding of a generalized process for separating the thermal and magnetic signal components from a readback signal, as well as several useful applications that exploit the availability of the thermal information signal, reference is made to FIG. 3 which illustrates in flow diagram form a method for obtaining and utilizing a thermal signal component of a readback signal in accordance with one embodiment of the present invention. At step 30, information is read from a magnetic storage disk by an MR element 72 to induce in the MR element 72 a readback signal that may appear to exhibit distortion or modulation, but in actuality contains a magnetic signal component and a thermal signal component. It should be noted that the magnitude of the magnetic signal component may be zero where no magnetic information has been written to the disk. The thermal signal component, however, is generally present due to a previously unknown phenomenon that has now been understood, characterized, and utilized by the inventors. The thermal signal component is separated or extracted from the readback signal at step 32. The magnetic signal component of the readback signal separated at step 32 often includes a D.C. baseline modulation that distorts the amplitude of the magnetic signal component.

At step 34, the baseline modulation in the magnetic signal is eliminated, thereby restoring the baseline of the magnetic signal. If the extracted thermal signal is to be used for servo control, as tested at decision step 36, the thermal signal is transmitted to the servo control and processed accordingly at step 38. If the magnetic signal is to be used for servo control, the restored magnetic signal is transmitted to the servo control at step 40. If it is desired to perform a head flyheight routine, as tested at decision step 42, the thermal signal is transmitted to an estimated flyheight processor at step 44. If it is desired to perform a disk surface analysis or screening, as tested at decision step 46, the thermal signal is transmitted to a disk surface analysis processor at step 48. Further, if the thermal signal is to be used to perform error recovery or predictive failure analysis (PFA), as tested at decision step 50, the thermal signal is transmitted to an error recovery processor at step 52.

Figure 4:
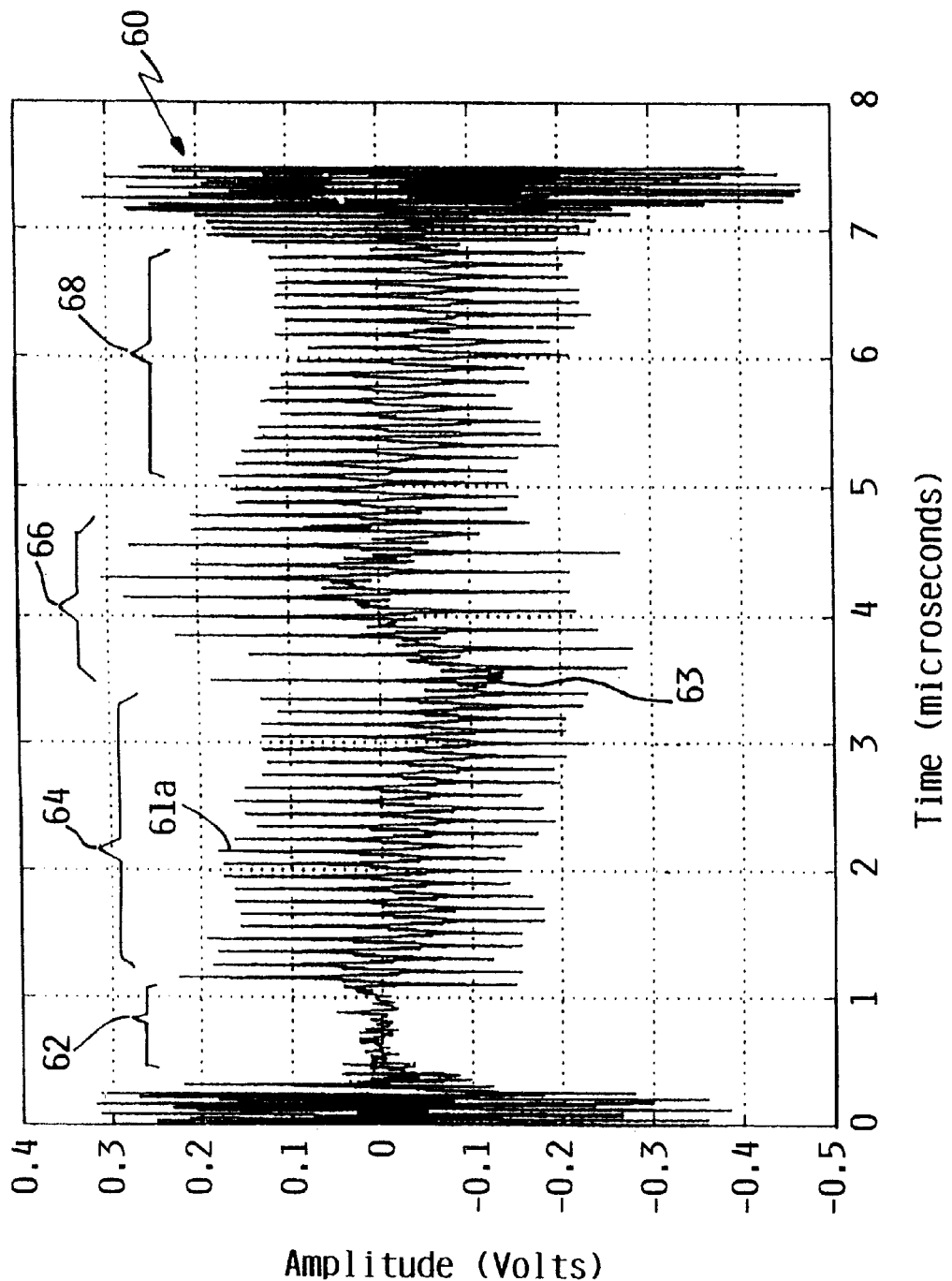
FIG. 4 is a showing of a readback signal induced in an MR head exhibiting a distorted D.C. baseline.
Figure 5:
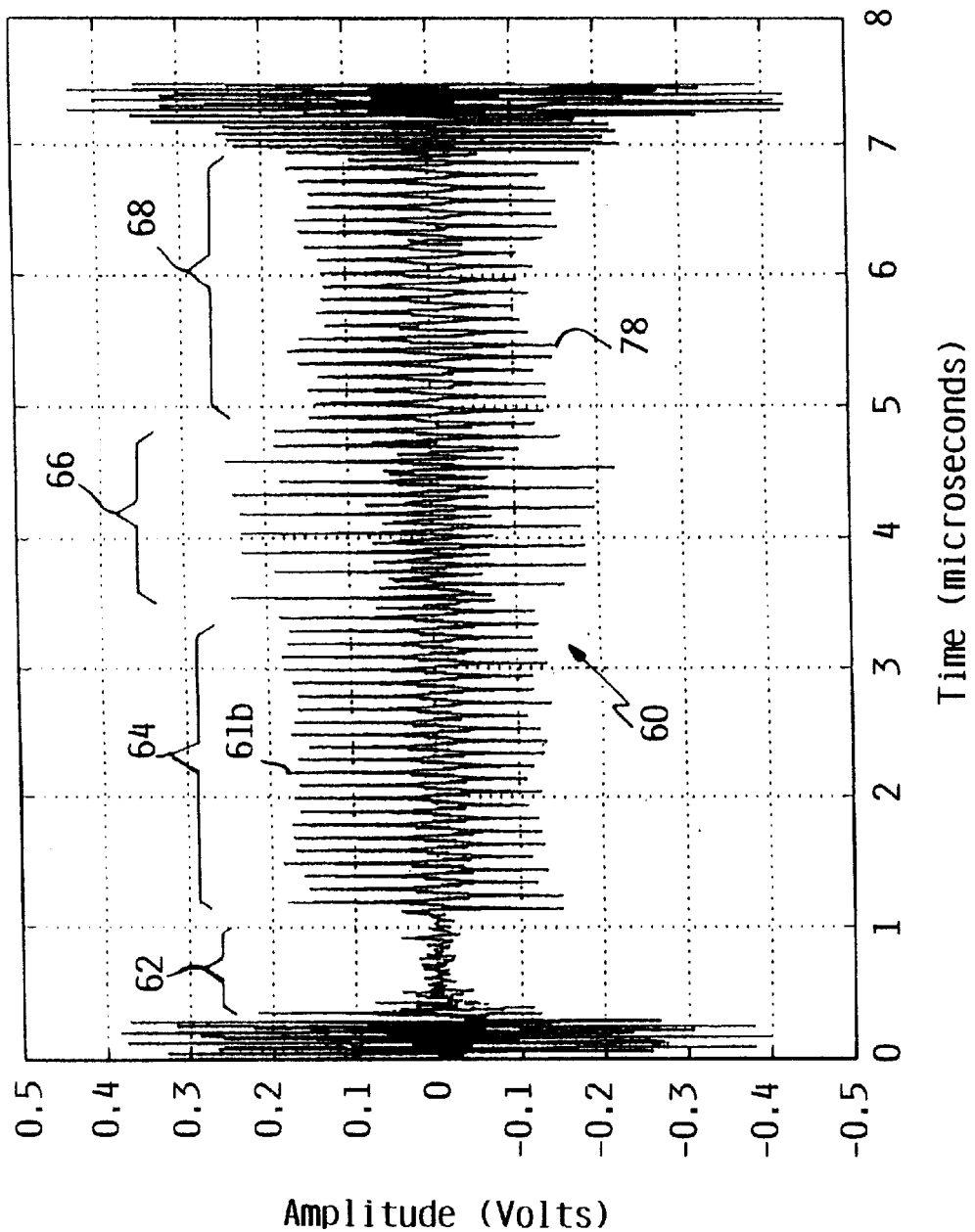
FIG. 5 is a showing of the readback signal of FIG. 4 exhibiting a restored D.C. baseline after being processed by a signal separation/modulation module.

Turning now to FIGS. 4 and 5, there is respectively illustrated a distorted readback signal and a non-distorted readback signal restored by a signal separation/restoration module 76 as shown in FIG. 1. All low frequency distortion (modulation), whether caused by thermal head-to-disk spacing activity or unwanted filtering from the AE module 74 or both, can be compensated for by the signal separation/restoration module 76. For the purpose of illustration, it is assumed that the readback signal 60 is a signal read from a servo sector on the data storage disk 24. In this example, the servo sector readback signal contains a number of information fields, namely, a write recovery field 62, a synchronization field 64, a Gray code field 66, and a burst pattern field 68. It is understood that the Gray code field 66 typically includes sector and cylinder identification fields.

It can be seen in FIG. 4 that the baseline of the servo control readback signal is severely distorted, and particularly so within the Gray code field 66. It is noted that the low frequency distortion associated with the Gray code field 66 is not caused by thermal head-to-disk spacing changes, but is instead caused by the highpass filtering nature of the AE module 74. The Gray code field 66 is typically amplitude detected which renders the sector and cylinder information difficult to reliably interpret in the presence of amplitude distortion. Such amplitude distortion, in turn, often introduces servo control errors of varying severity depending on the magnitude of the distortion. It is noted that such amplitude distortion in a readback signal 60 obtained from a data sector, in contrast to a servo sector readback signal, can similarly introduce detection and interpretation errors resulting in soft or hard read errors. It is not uncommon for up to 15%–20% of the sectors formatted on a disk 24 surface to demonstrate appreciable levels of readback signal distortion similar to that depicted in FIG. 4.

As discussed previously, the source of the undesirable readback signal 60 modulation has heretofore been misunderstood by those skilled in the art to result from noise in the MR element 72 or other source of MR element 72 instability or operational anomaly. The inventors, however, have discovered that the readback signal distortion may in addition be due to the presence of an independent thermal signal component of the readback signal that modulates the magnetic signal component 61a, thereby resulting in a readback signal 60 having a time-varying baseline. The signal separation/restoration module 76 processes the readback signal 60 to restore the readback signal baseline, as shown in FIG. 5, and to produce a virtually pure, magnetic signal 61b unperturbed by the thermal signal component.

Figure 6A:
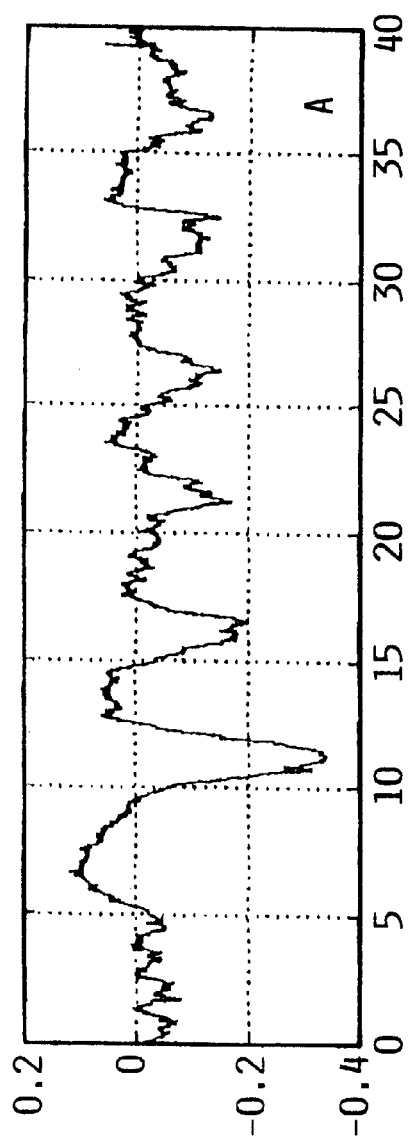
FIG. 6 is a showing of a thermal signal extracted from a readback signal induced in an MR element at a particular track location, and a readback signal obtained from the same track location after AC erasure of the magnetic information.
Figure 6B:
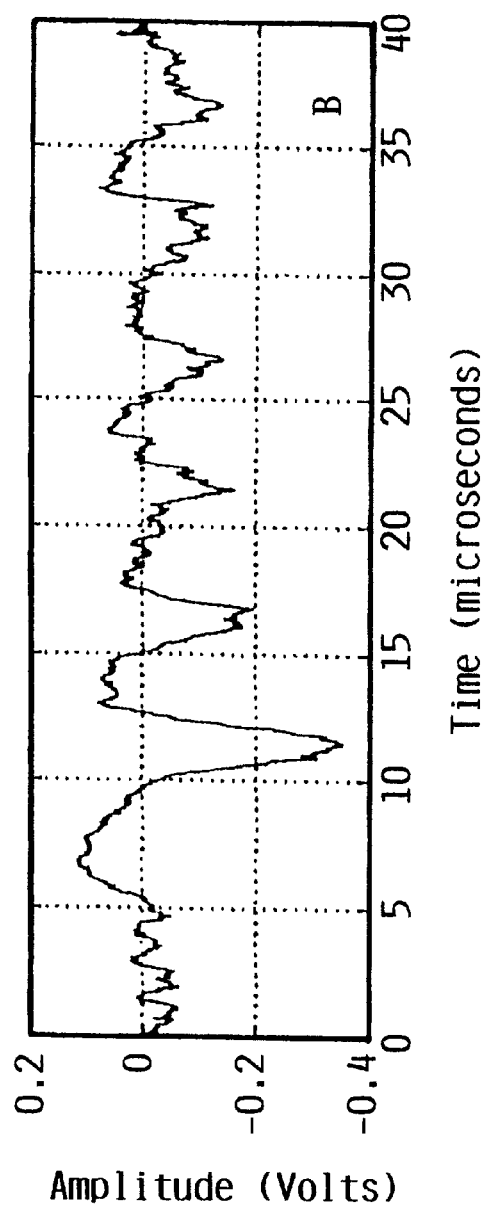

The independence of the magnetic signal and the thermal signal is demonstrated by the waveforms shown in FIG. 6. The waveform shown in FIG. 6(a) represents a thermal signal extracted from a magnetic readback signal using an MR head and a digital filter configured as a lowpass filter. After the waveform shown in FIG. 6(a) was obtained, the track from which the waveform was generated was subjected to a magnetic AC erasure. The same MR head was moved to the same location of the erased track to obtain the waveform shown in FIG. 6(b). It can be seen that the extracted thermal signal shown in FIG. 6(a) and the readback signal derived from the erased track shown in FIG. 6(b) are substantially identical. The two waveforms provided in FIG. 6 verify that two simultaneously read thermal and magnetic signals are present in the readback signal and that the signals are independent and separable.

Viewing the readback signal in terms of its two independent and separable components reveals a previously unappreciated informational content available in a readback signal obtained using an MR head. In particular, information about the surface of the disk can be derived from the thermal signal. An exaggerated side view of an MR slider 67 and MR element 72 in proximity with the surface 24a of a magnetic data storage disk 24 is illustrated in FIG. 7. The disk surface 24a has a generally varying topography at a microscopic level. As illustrated, a disk surface 24a may include various surface defects, such as a pit 122, a bump 124, or a surface portion 126 void of magnetic material. It is to be understood that surface features such as grooves, pits, and bumps, for example, may be purposefully provided on the disk surface 24a for purposes of encoding information on the disk surface 24a.

As illustrated in FIG. 7, the thermal response voltage level 119 of the MR element 72 changes as a function of the spacing, denoted by parameter y, between the MR element 72 and the disk surface 24a. Changes in the magnetic readback signal result from changes in the resistance of the MR element 72. More particularly, a typical MR element, which is a resistor that is sensitive to the presence of magnetic fields, is electrically coupled to a current source between positive and negative element leads. A bias current is applied to the MR element 72 via the leads. In normal operation, magnetic transitions on the disk surface 24a affect the resistance of the MR element 72 giving rise to voltage variations across the MR element 72. These voltages occur at the frequency of the magnetic data transitions recorded on the disk surface 24a and are the basis for the magnetic signal component of the readback signal.

The resistance of the MR element 72 is also effected by the head-to-disk spacing. More particularly, head-to-disk spacing changes result in concomitant changes in heat transfer from the MR element 72, which is heated by a constant bias current, to the disk 24. The heat transfer is an inverse function of the head-to-disk spacing. If the heat transfer from the MR element 72 is increased (small spacing), then the temperature of the MR element 72 and its resistance will decrease. The temperature and the resistance of the MR element 72 will increase (larger spacing) if the heat transfer is reduced. Thus, changes in the heat transfer between the MR element 72 and the disk 24 results in an alteration of the temperature of the MR element 72. Temperature changes in the MR element 72 result in corresponding changes in the electrical resistance of the MR element 72 and, therefore, the voltage across the MR element 72 being supplied by a constant bias current. It is noted that variations in slider flyheight typically occur at a frequency significantly lower than that of the magnetic transitions. Therefore, such temperature changes in the MR element 72 occur at a frequency significantly lower than the magnetic data transitions and are the basis of the thermal component of the readback signal.

As FIG. 7 illustrates, there is an inverse relationship between the topographical surface variations of the disk 24 and the changes in magnitude of the thermal signal 119. As the instantaneous head-to-disk spacing (y) increases, there results a corresponding increase in air space insulation between the MR element 72 and the disk surface 24a, thereby causing an increase in the temperature in the MR element 72. This temperature increase in the MR element results in a corresponding increase in the MR element 72 resistance due to the positive temperature coefficient of the MR element material typically used to fabricate the MR element 72. Permalloy, for example, is a preferred material used to fabricate the MR element 72 and demonstrates a temperature coefficient of $+3 \times 10^{-3}/°$ C. An MR element 72 passing over a bump 124 on the disk surface 24a, by way of example, results in increased heat transfer occurring between the MR element 72 and the disk surface 24a, thereby causing cooling of the MR element 72. Such cooling of the MR element 72 causes a decrease in the MR element resistance which, in turn, results in a corresponding decrease in the voltage $v_{TH}$ across the MR element 72 at a constant bias current.

As a result of the above-described interaction between the MR element 72 and the disk surface 24a, it can be seen by referring to the pit 122 depicted on the disk surface 24a that the thermal voltage signal $v_{TH}$ 119 across the MR element 72 increases in amplitude as a function of increasing head-to-disk separation distance (y). It can further be seen by referring to the bump 124 depicted on the disk surface 24a that the thermal voltage signal $v_{TH}$ 119 decreases in amplitude as a function of decreasing head-to-disk separation distance. For purposes of convenience, it may be desirable to invert the thermal voltage signal $v_{TH}$ 119 so that changes in disk surface 24a topography correspond directly, rather than inversely, to changes in the thermal voltage signal $v_{TH}$ 119. Thus, the negative value of the MR head voltage, —$v_{TH}$, will provide a qualitative indication of the disk surface 24a topography by indicating "cooling areas" as peaks and "heating areas" as valleys.

Also shown in FIG. 7, is a magnetic spacing signal 121 which has been conditioned to correspond to variations in the disk surface 24a. It can be seen that the magnetic spacing signal 121 incorrectly indicates the presence of some surface features, such as magnetic voids 126, as variations in the topography of the disk surface 24a. It can further be seen that the magnetic spacing signal 121 provides an inferior indication of other surface features, such as bumps 124, when compared to disk surface imaging information provided by use of the thermal signal 119.

It should be appreciated that the thermal signal contains in general a representation of the thermal response of the MR element as it interacts with the disk. If the emissivity or absorptivity of the surface of the disk were to vary, the resultant thermal signal would accordingly vary. As will be better appreciated from the discussion below, variations in the disk surface, such as surface profile or emissivity/absorptivity, may be purposefully introduced and exploited by using the informational content of both components of the readback signal.

Figure 8:
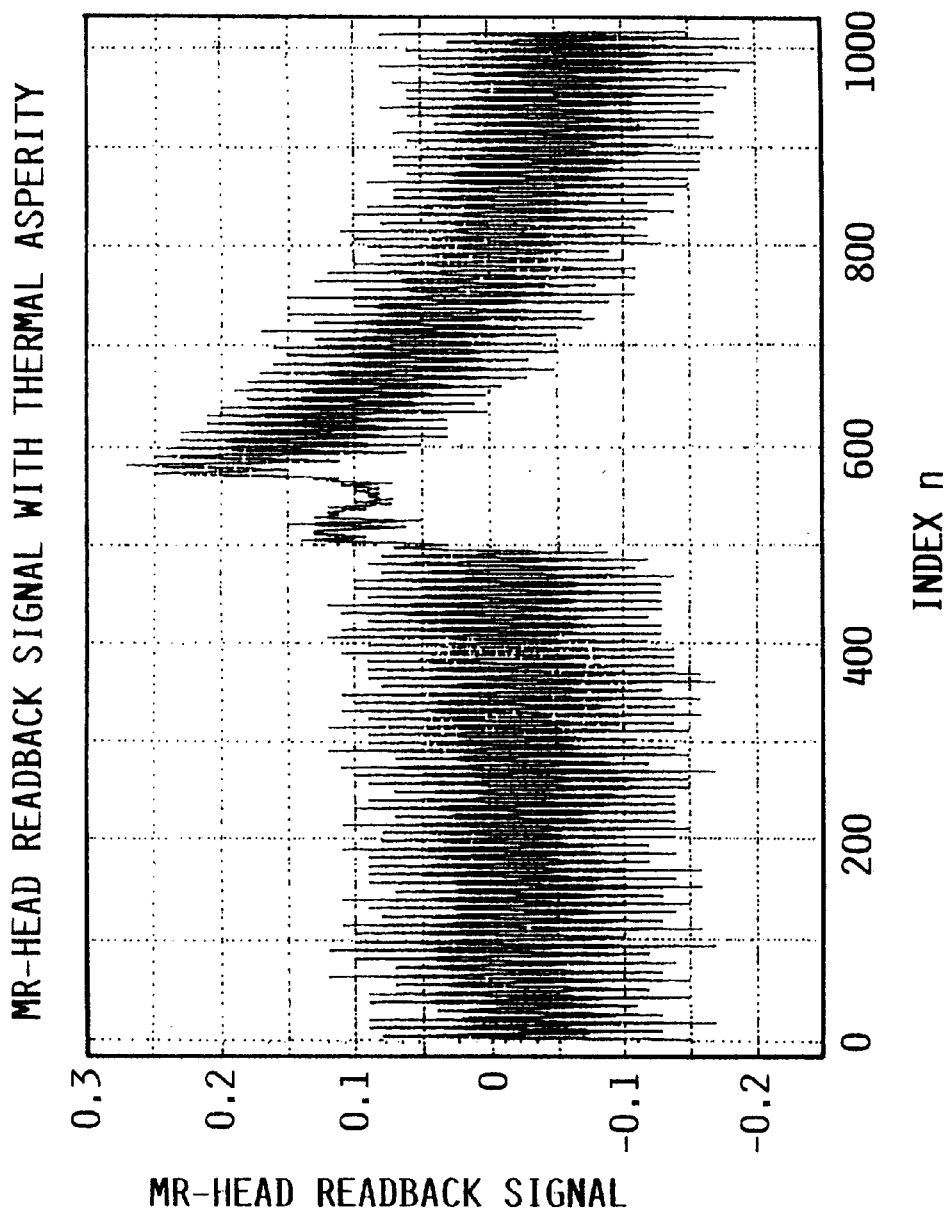
FIG. 8 is a showing of a readback signal indicating a head-to-disk contact event.

Another characteristic of an MR element 72 that influences the nature of the readback signal obtained from the disk surface concerns a situation whereby the MR element 72 comes into physical contact with the disk surface or other obstruction. A thermal asperity (TA), for example, occurs when a temporary physical contact occurs between the disk surface and the MR element 72. The negative (cooling) peak of the thermal voltage response to a bump 124, for example, is suddenly replaced by a large, but narrow, positive spike response followed in rapid succession by the negative cooling response as shown in FIG. 8. The positive spike response is caused by mechanical frictional heating between the MR element 72 and the local asperity on the disk surface 24a. Due to the mechanical friction associated with a thermal asperity, the magnetic coating can be scraped off in the area of physical contact. This will result in a magnetic void 126, but is not the only source of such voids.

Figure 9:
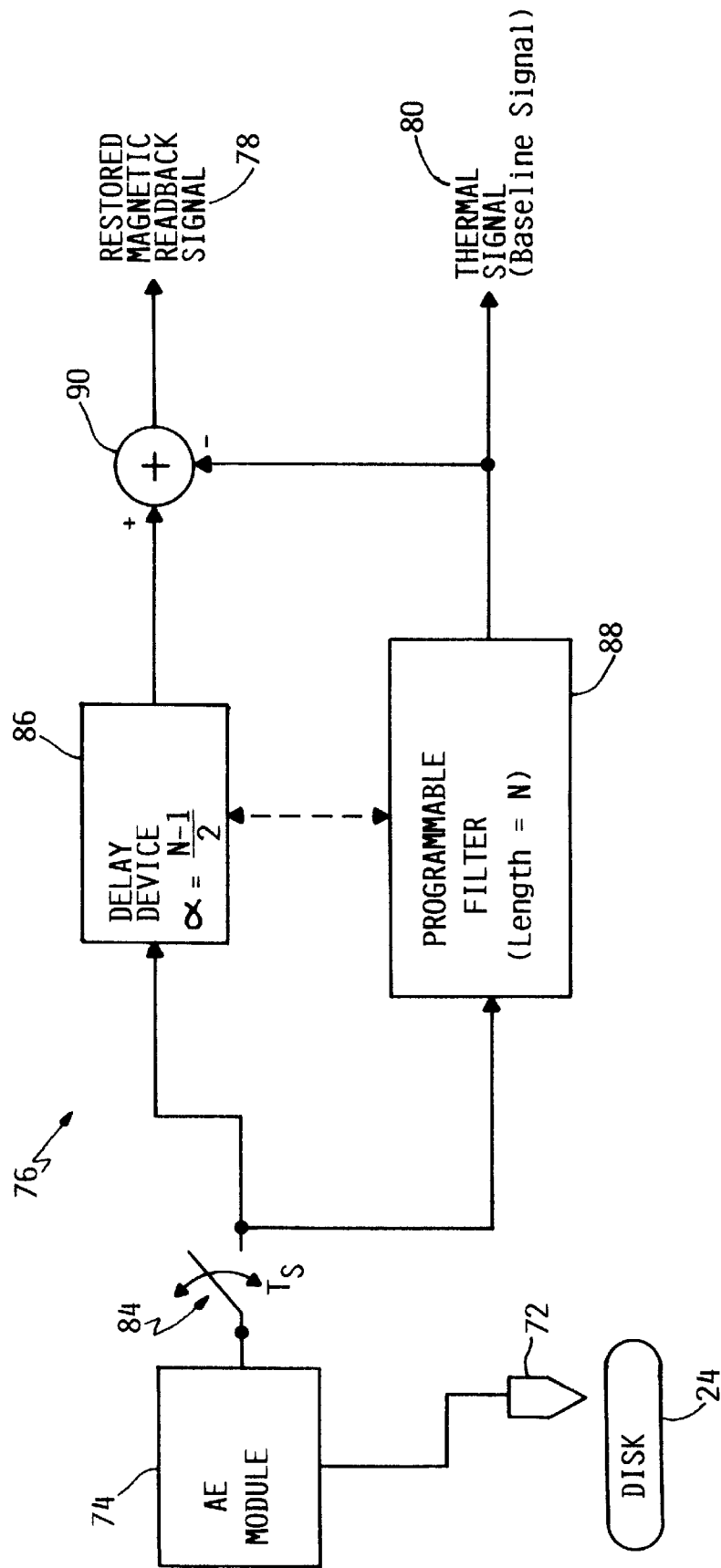
FIG. 9 is a block diagram of a signal separation/modulation module for extracting a thermal signal and a magnetic signal from a readback signal induced in an MR element, and for restoring the D.C. baseline of the magnetic signal.

Referring to FIG. 9, there is illustrated an embodiment of a signal separation/restoration module 76 discussed previously with respect to FIG. 1. It is to be understood that the signal separation/restoration module 76 may be employed to perform the single task of separating the magnetic signal from the readback signal in order to remove the low frequency modulation component of the readback signal attributed to thermal signal influences or other causes. In another embodiment, the signal separation/restoration module 76 may be employed to perform the dual tasks of separating the magnetic signal component from the readback signal 60 to remove low frequency thermal signal component, and, in addition, extracting the thermal signal from the readback signal, thus making available for subsequent processing the informational content of both the magnetic signal and thermal signal in substantially independent form.

As shown in FIG. 9, a readback signal is induced in the MR element 72 situated in close proximity with a magnetic data storage disk 24. As will be discussed in greater detail hereinbelow, the readback signal modulation varies in frequency and amplitude as a function of thermal signal component behavior.

In one embodiment, a readback signal received from the AE module 74 from the MR element 72 is converted from analog form to digital form by an analog-to-digital converter 84. The digitized readback signal is then communicated to a delay device 86 and to a linear phase programmable filter 88. The programmable filter 88 is a finite impulse response (FIR) filter having a length N, where N represents the number of impulse response coefficients or taps of the programmable filter 88. The readback signal applied to the input of the programmable filter 88 is subject to a total signal delay corresponding to the length N of the programmable filter 88 as the readback signal passes through the programmable filter 88.

In accordance with this embodiment, the programmable filter 88 is programmed with appropriate tap coefficients and weights so as to pass the relatively low frequency thermal signal component of the readback signal and to filter out the relatively high frequency magnetic signal component. As such, the programmable filter 88 is configured as a lowpass filter and programmed to pass the thermal signal content which can be generally characterized as a medium frequency signal with much of its energy in the frequency range of approximately 10 kilohertz (KHz) to approximately 100–200 KHz. It is noted that the magnetic signal component of the readback signal has a frequency ranging between approximately 20 megahertz (MHz) and 100 MHz. The thermal signal 80 at the output of the programmable filter 88 is communicated to a signal summing device 90. From the output of the programmable filter 88, the thermal signal 80 may be transmitted to other components in the data storage system, such as to a servo control for purposes of controlling track following and track seeking operations.

The delay device 86 receives the readback signal 60 from the analog-to-digital converter 84 and delays the transmission of the readback signal to the signal summing device 90 by a duration of time equivalent to the delay time required for the readback signal to pass through the programmable filter 88. As such, the readback signal, containing both magnetic and thermal signal components, and the thermal signal 80, extracted from the readback signal by the programmable filter 88, arrive at the signal summing device 90 at substantially the same time. The signal summing device 90 performs a demodulation operation on the readback signal and thermal signal 80 to produce a restored readback signal 78. Thus, the signal separation/restoration module 76 illustrated in the embodiment depicted in FIG. 9 provides for the separation of the magnetic and thermal signal components of a composite readback signal and, additionally, produces a non-distorted restored magnetic readback signal 78.

Figure 10:
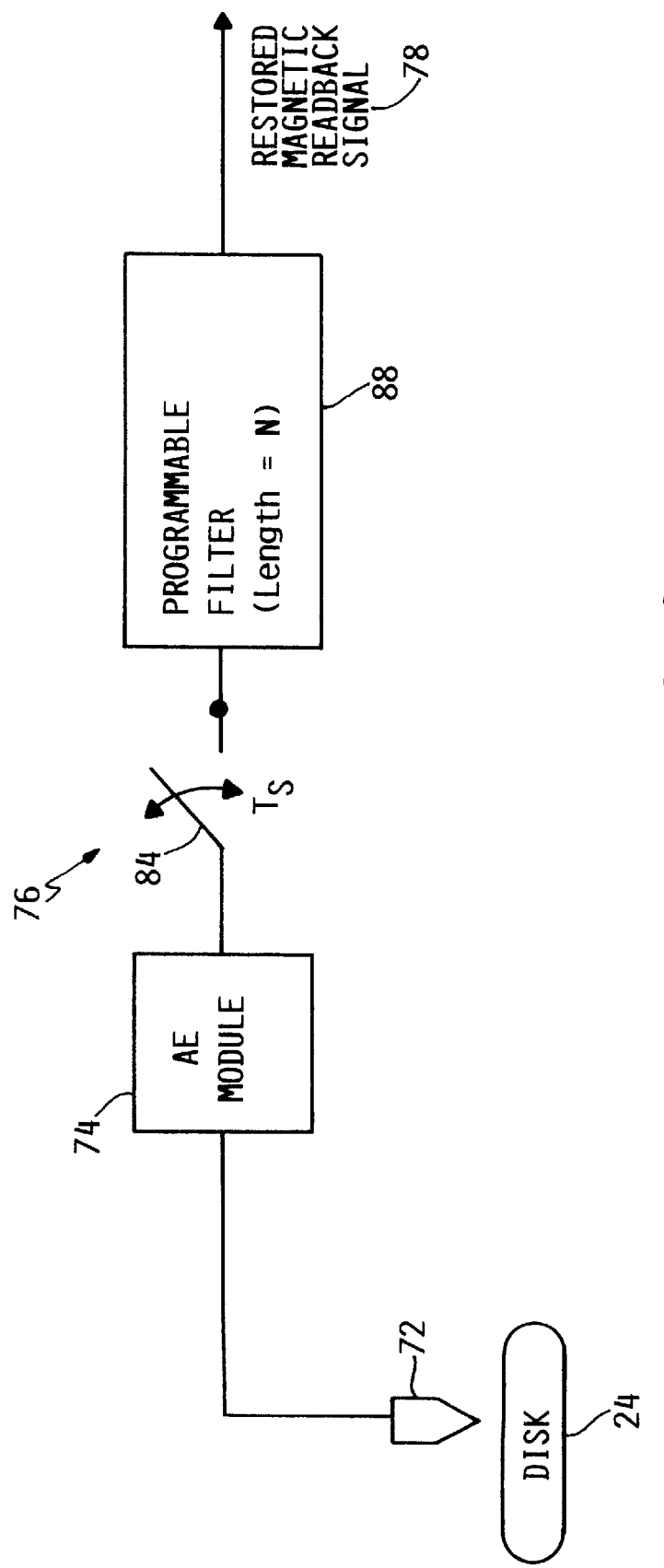
FIG. 10 is a block diagram of a signal separation/modulation module for restoring the D.C. baseline of a magnetic readback signal.

In FIG. 10, there is illustrated another embodiment of a signal separation/restoration module 76 in which a restored magnetic readback signal 78 is produced after processing a modulated readback signal through the signal separation/restoration module 76. In accordance with this embodiment, an amplitude-distorted readback signal containing magnetic and thermal signal components is sensed by an MR element 72 from a magnetic data storage disk 24 and communicated to an AE module 74. The modulated readback signal is then digitized by a sampler 84 and then passed through an appropriately configured programmable filter 88 to produce a non-distorted restored magnetic readback signal 78. The programmable filter 88 is preferably a finite infinite response (FIR) filter programmed to pass the relatively high frequency magnetic signal component of the composite readback signal, while rejecting the relatively low frequency thermal signal component of the composite readback signal. Although a filter other than a FIR filter may be employed as the programmable filter 88, it is important that the filter 88 have a substantially perfect linear phase response in order to achieve optimal performance. This is readily achieved using a digital FIR filter. In some applications, however, some degree of non-linear phase behavior of the filter 88 may be tolerated.

In general, when a signal passes through a filter, it is modified in amplitude and/or phase. The nature and extent of the modification of the signal is dependent on the magnitude and phase characteristics of the filter. The phase delay or group delay of the filter provides a useful measure of how the filter modifies the phase characteristics of the signal. A filter with a non-linear phase characteristic will introduce a phase distortion in the signal that passes through it. Such phase distortion is introduced because the frequency components in the signal will each be delayed by an amount not proportional to frequency, thereby altering their harmonic relationships. It has been found that a certain class of FIR filters provide for perfect linear phase response which is necessary to eliminate virtually all of the undesirable modulation of a readback signal resulting from the influence of the thermal signal component, and to produce a restored magnetic readback signal 78.

Figure 11A:
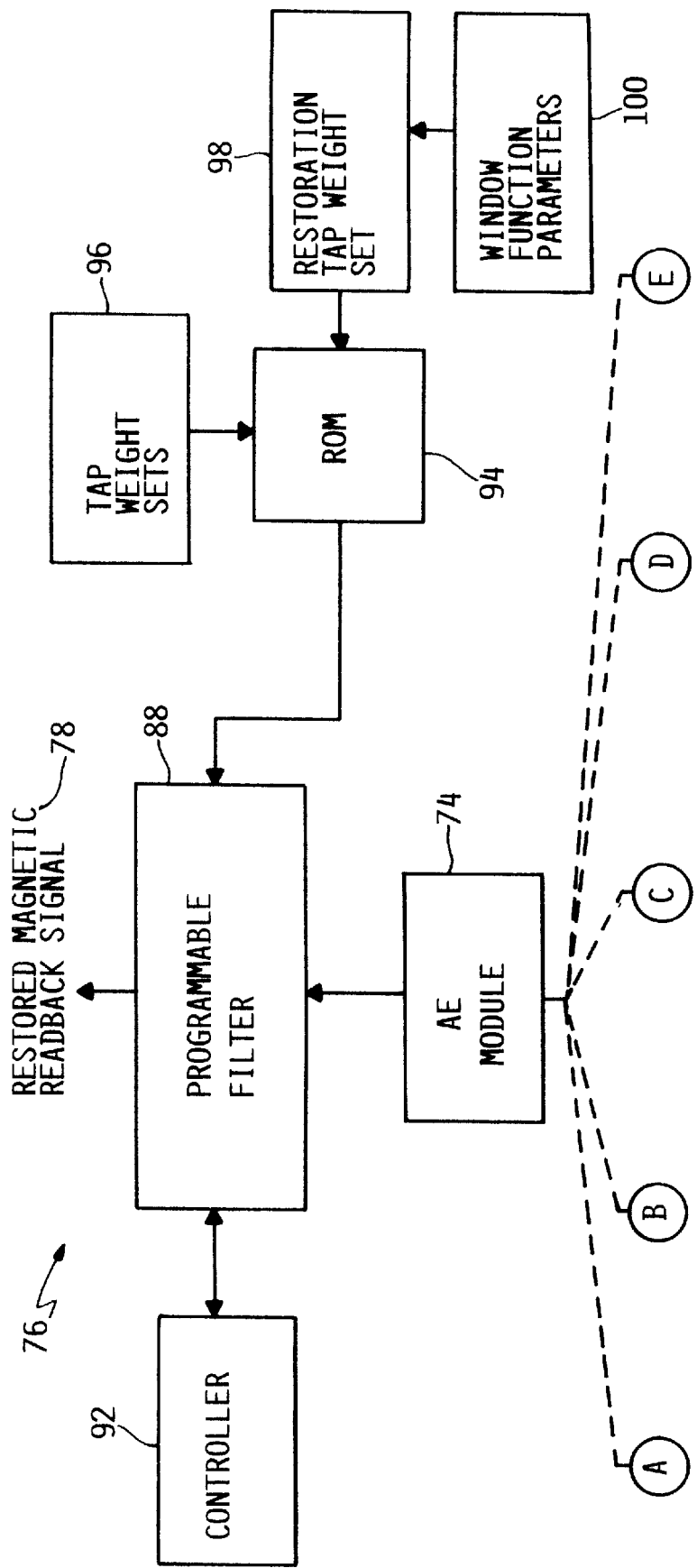
FIG. 11 is a block diagram of a system for selectively communicating a readback signal to a signal separation/restoration module.
Figure 11B:
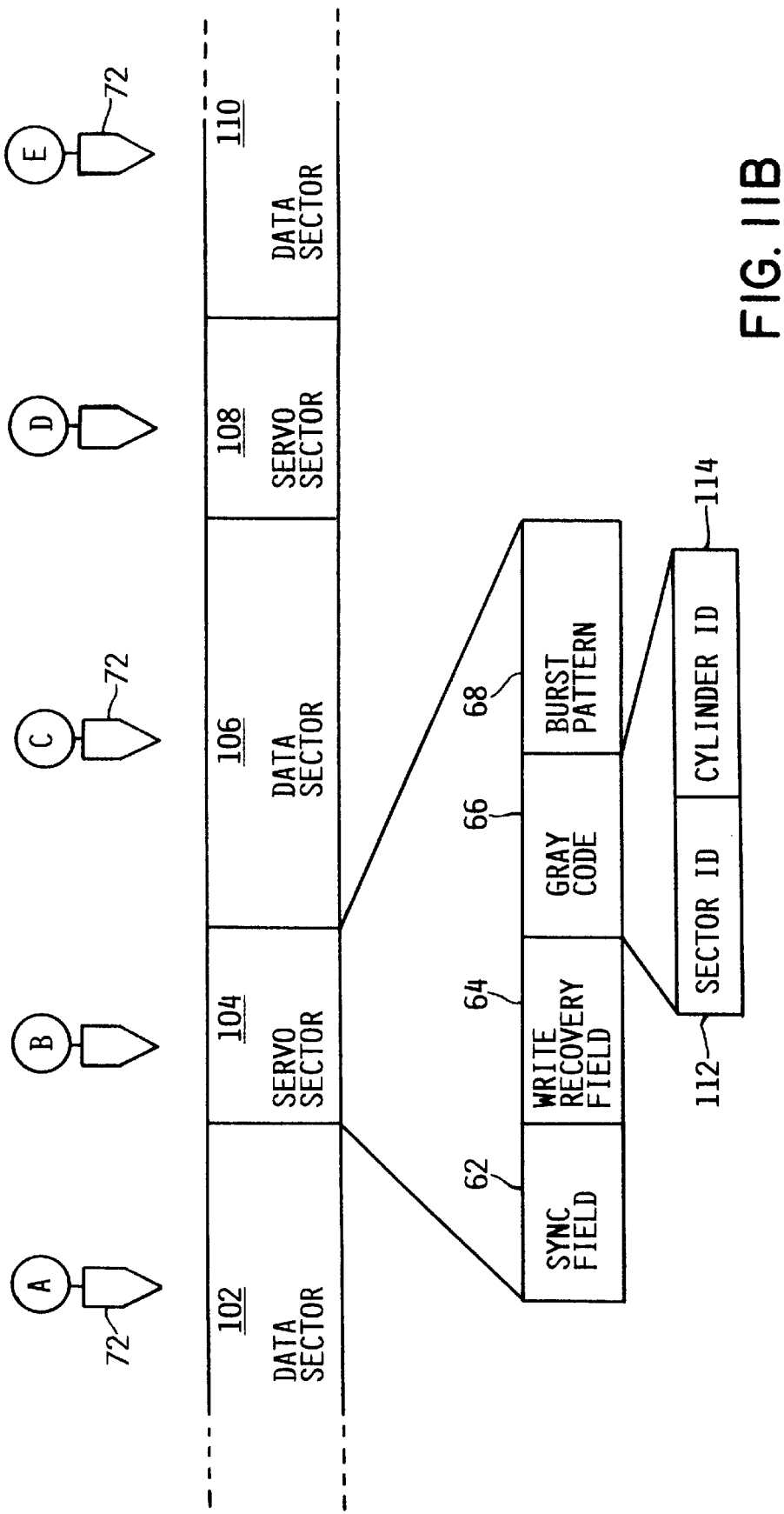

Referring to the embodiments illustrated in FIG. 11, there is depicted a capability to selectively couple and decouple the signal separation/restoration module 76 from the recording channel through which a readback signal typically passes. The programmable filter 88 is shown coupled to a read-only-memory (ROM) 94 within which is stored a number of programmable filter parameter sets. In an embodiment employing a FIR filter 88, the ROM 94 typically stores a number of tap weight sets 96 and may additionally store at least one restoration tap weight set 98. By way of example, it is assumed for purposes of illustration that the recording channel for a particular data storage system includes a single 10-tap FIR filter 88. The 10-tap FIR filter 88 is coupled to a ROM 94 which is configured to store 64 different sets of tap weights 96, any of which may be loaded into the FIR filter 88 for purposes of reprogramming its response. As discussed previously, a modulated magnetic readback signal read from a servo sector can produce particularly deleterious results when the servo controller attempts to process the distorted readback signal. Sector and cylinder information contained in the Gray code field 66 of the servo sector, for example, may be misinterpreted or unreadable.

The signal separation/restoration module 76 can selectively be utilized so as to process readback signal information only from servo sectors embedded between data sectors as shown in FIG. 11. In accordance with this embodiment, a single programmable filter 88 employed in a recording channel of a data storage system can be time-shared between processing readback signals corresponding to servo sectors through the signal separation/restoration module 76 and servo channel, and processing readback signals corresponding to data sectors through the data channel. When reading data sector information, the readback signal is selectively passed through the data channel so as to bypass the signal separation/restoration module 76.

As depicted in FIG. 11, and in accordance with an embodiment of a data storage disk 24 employing an embedded servo architecture, an alternating series of data and servo sectors will pass under the MR element 72 as the data storage disk 24 rotates, typically at several thousand RPM. When the MR element 72 is reading information from a data sector 102, the readback signal produced in the MR element 72 is transmitted to the AE module 74, the FIR filter 88, and to the data channel so as to bypass the signal separation/restoration module 76. It is noted that the FIR filter 88 is programmed with one of several tap weight sets 96 when processing the signal information acquired from the data sector 102.

As the servo sector 104 comes into proximity with the MR element 72, a restoration tap weight set 98 stored in the ROM 94 is loaded into the FIR filter 88, thereby replacing the previously loaded tap weight set residing in the FIR filter 88. The restoration tap weight set 98 configures the FIR filter 88 to remove the thermal signal component of the readback signal read from the servo sector 104, and produces a restored magnetic readback signal 78 corresponding to the pure magnetic signal stored in the servo sector 104. The restored magnetic readback signal 78 is then communicated to the servo control and processed accordingly. As the data sector 106 adjacent the servo sector 104 comes into proximity with the MR element 72, a selected tap weight set 96 is loaded into the FIR filter 88 so as to replace the previously loaded restoration tap weight set 98. The readback signal derived from the data sector 106 is processed through the FIR filter 88 and data channel so as to bypass the signal separation/restoration module 76. The process of selectively processing the readback signal derived from servo sectors is repeated in a similar manner.

It is to be understood that the embodiment illustrated in FIG. 11 is particularly well-suited for retrofitting a data storage system that includes a single programmable filter 88 in the read/write channel. It can be appreciated that incorporating an additional programmable filter may be desirable so that a first programmable filter is configurable for operation in the servo channel, while a second programmable filter is configurable for operation in the data channel. In accordance with a configuration employing two such independent programmable filters, restoration of readback signals derived from data sectors can result in an improved error rate performance of the data storage system.

It is noted that the process of loading the restoration tap weight set 98 stored in ROM 94 into the programmable filter 88 may be performed upon detection of a synchronization (sync) field 64 or other signal indicating the beginning of a servo sector. Similarly, a sync field or other information signal indicative of the beginning of a data sector can be sensed for determining when a tap weight set 96 for a data sector is to be loaded into the programmable filter 88 for purposes of reading information from data sectors. For more details on designing, implementing, and programming a FIR filter suitable for use in the signal separation/restoration module 76, reference is made to E. C. Ifeachor, B. W. Jervis, "Digital Signal Processing" (Addison-Wesley Publishing Company, Inc. 1993).

Returning to FIGS. 4 and 5, the modulated readback signal shown in FIG. 4 represents the appearance of the readback signal prior to being processed by the signal separation/restoration module 76. The representation of the readback signal in FIG. 5 illustrates the readback signal of FIG. 4 after being processed by the signal separation/restoration module 76. The undesirable influence of the thermal signal component on the readback signal shown in FIG. 4 was eliminated by employing a 9-tap FIR filter in the signal separation/restoration module 76 in order to produce the restored magnetic readback signal 78 shown in FIG. 5. The magnitude and phase characteristics of the 9-tap FIR filter utilized to produce the restored magnetic readback signal 78 shown in FIG. 5 are illustrated in FIG. 12.

Figure 13A:
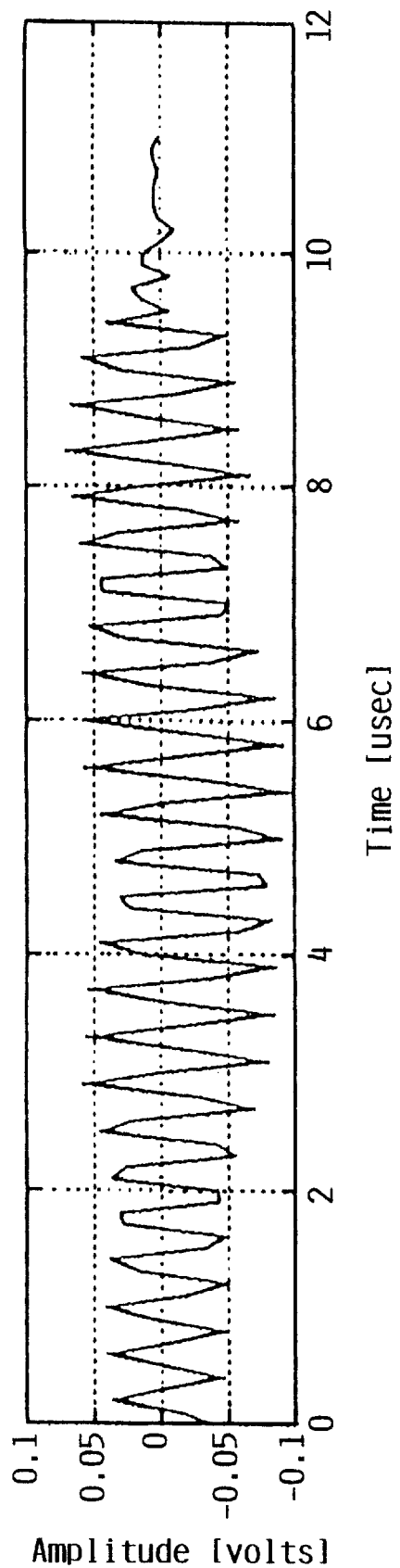
FIGS. 13($a$), 13($b$), and 13($c$) respectively illustrate a readback signal induced in an MR head, a restored magnetic signal component of the readback signal, and an unrestored magnetic signal component of the readback signal.
Figure 13B:
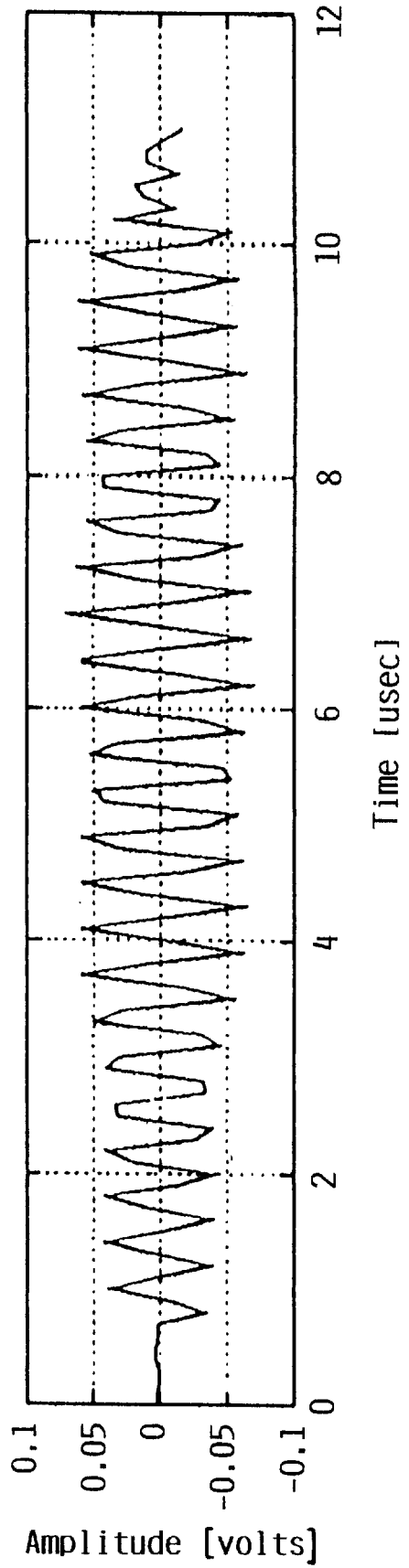

In particular, it can be seen in FIG. 12(b) that the 9-tap filter exhibits perfect linear phase response over the frequency range of interest. The effectiveness of the 9-tap FIR filter in eliminating the baseline shift or modulation of the readback signal is demonstrated in FIG. 13. FIG. 13(a) shows a readback signal demonstrating an unstable or amplitude-varying baseline. In FIG. 13(b), the modulating baseline of the readback signal apparent in FIG. 13 (a) has been eliminated after passing the distorted readback signal through an appropriately programmed 9-tap FIR filter. The tap weights for the 9-tap filter used to restore the baseline of the readback signal was defined to include tap weights of:

$$B(i)=(\tfrac{1}{9})*(-1, -1, -1, -1, 8, -1, -1, -1, -1),$$

or $$B(i)=(-0.111, -0.111, -0.111, -0.111, 0.889, -0.111, -0.111, -0.111, -0.111)$$

Figure 13C:
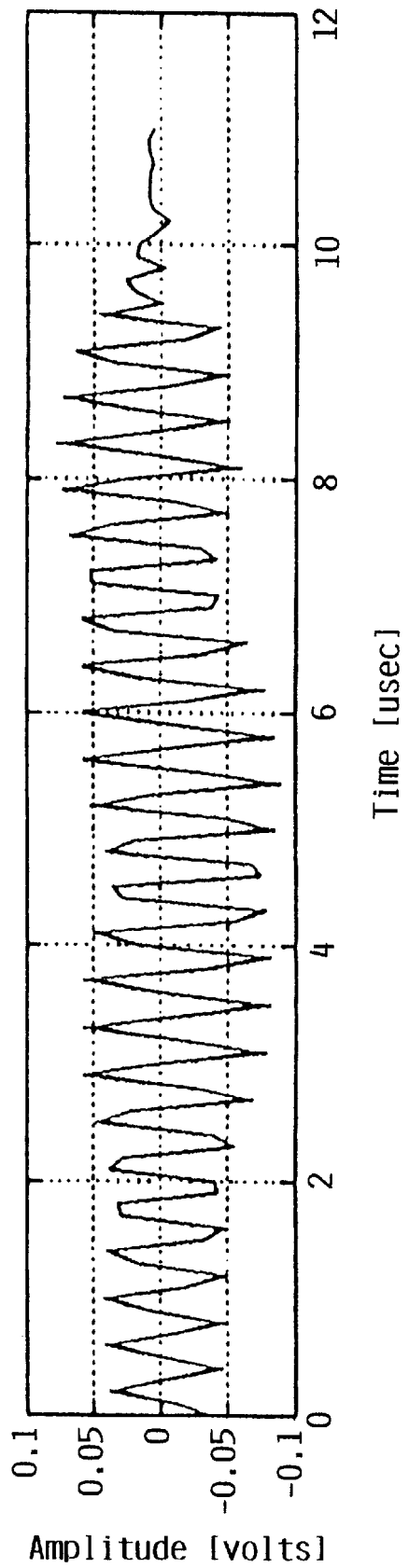

It is noted that the waveform shown in FIG. 13(c) was produced by passing the modulated readback signal shown in FIG. 13(a) through a conventional highpass Butterworth filter. It can be seen that undesirable modulation of the baseline of the readback signal is still present after passing the readback signal through a conventional highpass filter.

As previously indicated, the magnitude and phase characteristics of the 9-tap FIR filter used to restore the baseline of the readback signal as shown in FIG. 13(b) are respectively shown in FIGS. 12(a) and 12(b). It can be seen in FIG. 12(a) that some degree of ripple may occur in the passband of the filter which may be eliminated by applying a window function to the tap weights of the 9-tap FIR filter. By way of example, a Hamming window can be applied to the tap weights of the 9-tap FIR filter to produce a windowed restore filter having the following tap weights:

$$B(i)=(-0.0089, -0.0239, -0.06, -0.0961, 0.8889, -0.0961, -0.06, -0.0239, -0.0089)$$

Figure 14A:
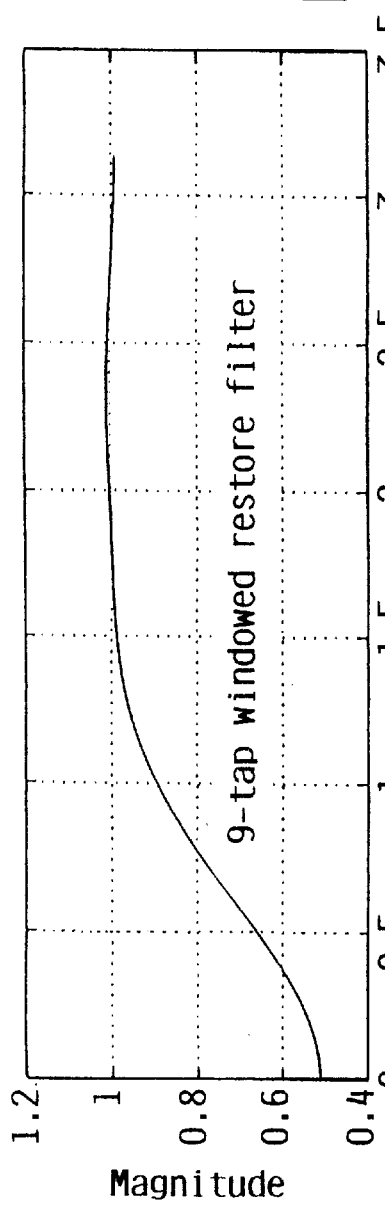
FIG. 14 illustrates the magnitude and phase response of a windowed FIR filter used in a signal separation/restoration module.
Figure 14B:
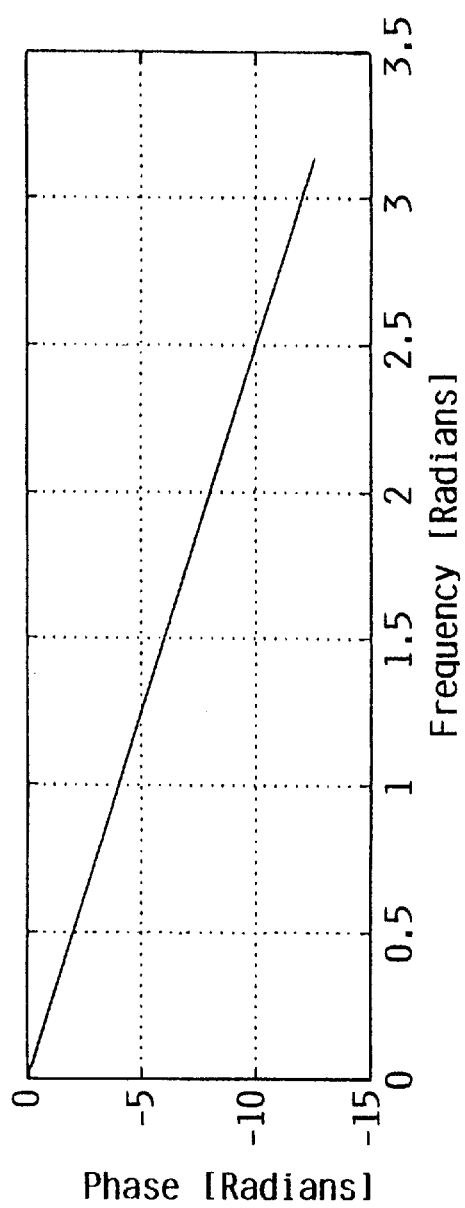

The output of the 9-tap windowed FIR filter having the above-listed tap weights results in the elimination of the ripple as shown in FIG. 14(a). As further shown in FIG. 14(b), the windowed 9-tap FIR filter retains its perfect linear phase response. It is noted that applying a window function, such as a Hamming window, to the tap weights of the programmable FIR filter 88 allows for a non-zero DC gain and some increase in low frequency response.

Turning now to FIGS. 15–22, there is illustrated another embodiment of a signal separation/restoration module 76 that is particularly well-suited for data storage systems that employ highpass filtering of a readback signal acquired from a magnetic data storage disk 24 using an MR element 72. This embodiment can be employed in newly designed data storage systems as well as retrofitted systems. In the design of an analog AE module 74, such as the AE module 74 illustrated in FIG. 1, it is often desirable to include highpass filtering in conjunction with a preamplifier for purposes of rejecting signal content of a readback signal below the frequency range of the magnetic signal component. The highpass filtering behavior of the AE module 74 distorts both in amplitude and phase the thermal signal component of the composite readback signal. This thermal signal distortion varies in severity depending on the frequency and phase response of the particular AE module employed.

By way of example, a highpass filter suitable for use in an AE module 74 may have a cutoff frequency of approximately 500 KHz and exhibit non-linear phase behavior. The frequencies associated with meaningful thermal signal information, however, are typically below 200 KHz, and typically range between 10 KHz to approximately 100 KHz. It can be appreciated that a highpass filter having a cutoff frequency of approximately 500 KHz will significantly distort the amplitude and phase of the thermal signal component of the readback signal. The magnetic signal component of the readback signal, however, remains unaffected by the highpass filter since the frequency range for the magnetic signal is generally some 20 to 40 times that of the highpass filter cutoff frequency.

Figure 15A:
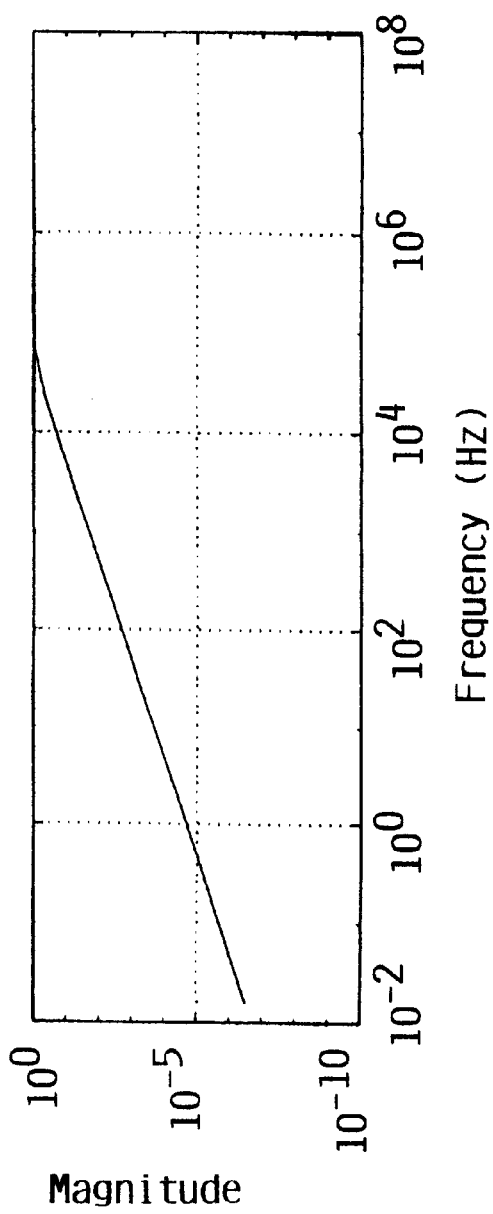
FIG. 15 is a showing of the magnitude and phase response of the highpass filtering behavior of a typical AE module.
Figure 15B:
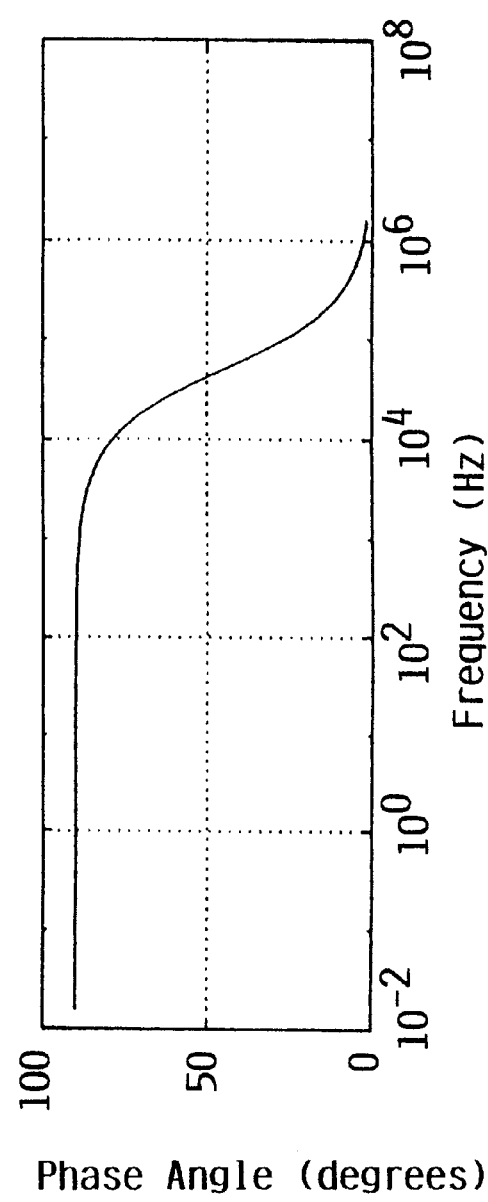

In FIGS. 15(a) and 15(b), there is respectively illustrated graphs showing the magnitude and phase response of a typical analog AE module 74 exhibiting a highpass filtering behavior. The highpass filter has a cutoff frequency of approximately 500 KHz. The digital equivalent of the analog transfer function of the effective highpass filter of the AE module 74 having a single pole at 500 KHz and the magnitude and phase response illustrated in FIG. 15 can be defined as:

$$H = \frac{b_h(1) + b_h(2) \cdot z^{-1}}{1 + a_h(2) \cdot z^{-1}} \qquad [1]$$

where:

$b_h(1)=0.9876$ $b_h(2)=-0.9876$ $a_h(2)=-0.9752$

The distortion in amplitude and phase of a thermal signal introduced by the highpass filtering behavior of the AE module 74 is effectively eliminated by use of an inverse filter having a transfer function inverse to that of the highpass filter. Passing the readback signal output from the AE module 74 through the inverse filter restores the thermal signal to its original form, both in amplitude and phase. For example, the transfer function of an inverse filter for conditioning a readback signal passed through a highpass filter having the above-described transfer function of equation [1] is given by:

$$H^{-1} = \frac{1 + a_h(2) \cdot z^{-1}}{b_h(1) + b_h(2) \cdot z^{-1}} \qquad [2]$$

Figure 16:
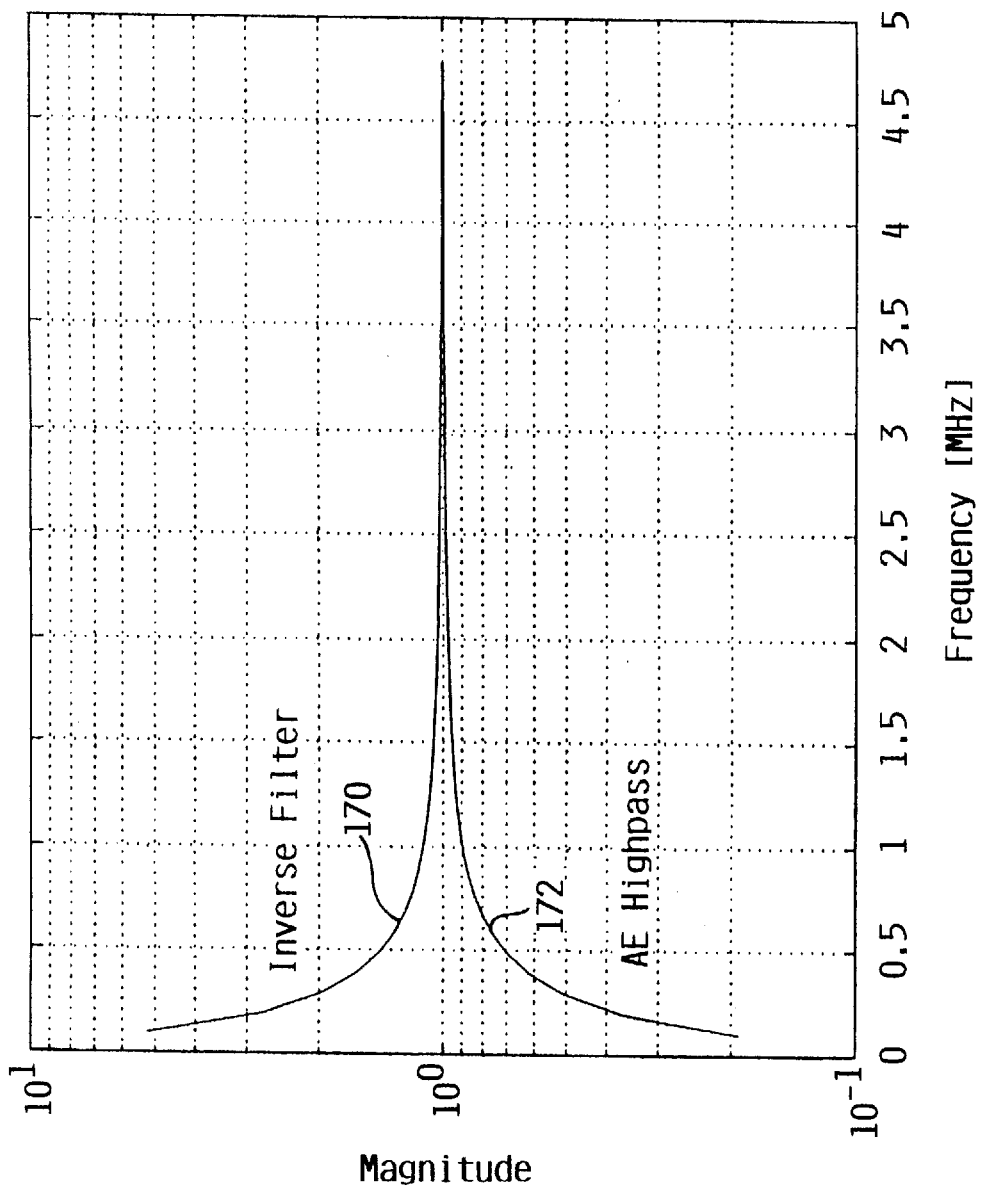
FIGS. 16 and 17 respectively show a comparison of the magnitude and phase response of the highpass filtering behavior of a typical AE module and an inverse filter having a transfer function inverse to that of the effective highpass filter of the AE module.
Figure 17:
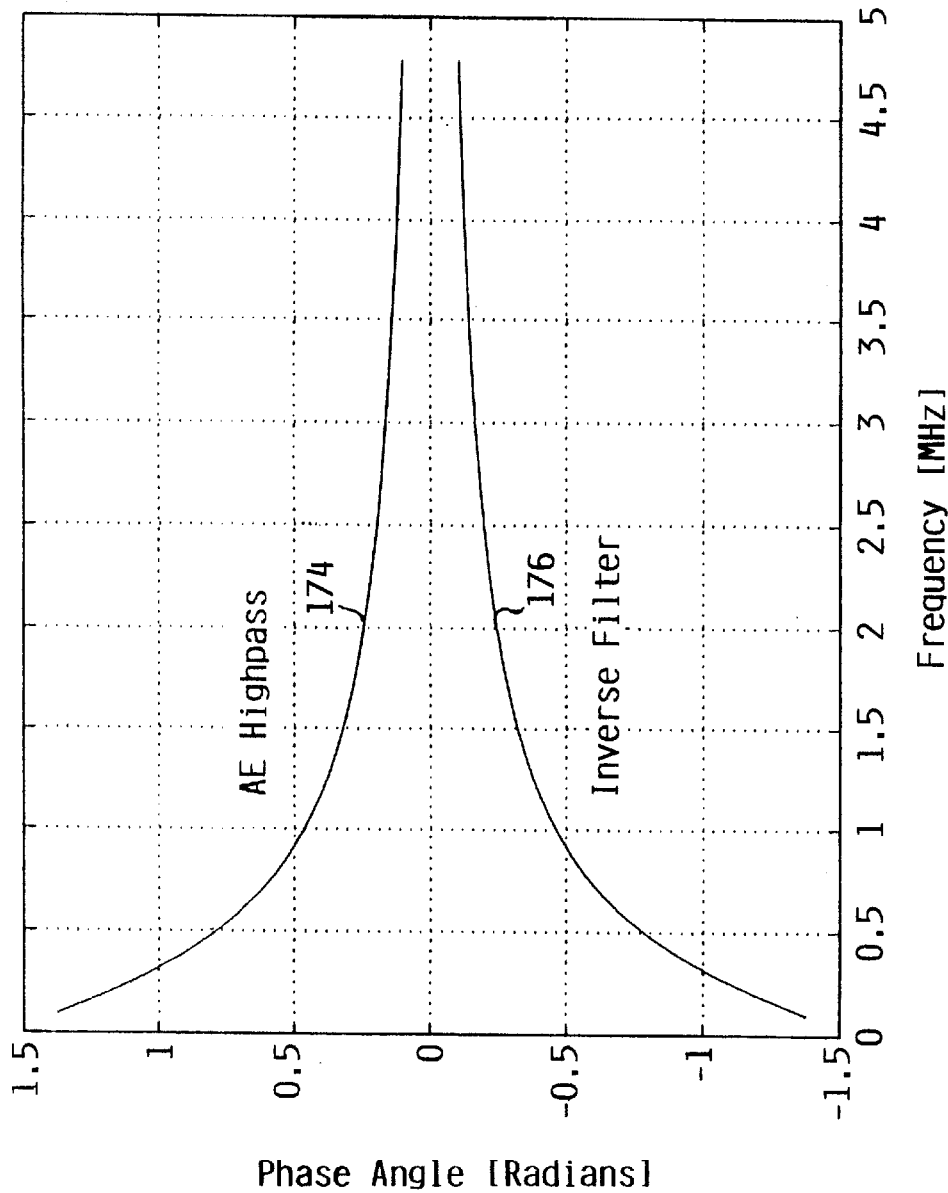

The magnitude and phase response for the effective highpass filter of the AE module 74 and the inverse filter described above in equation [2] are respectively plotted in FIGS. 16 and 17. In particular, the magnitude response of the inverse filter and the effective highpass filter of the AE module 74 is respectively shown as curves 170 and 172 in FIG. 16. The phase response of the inverse filter and the effective highpass filter is respectively shown as curves 176 and 174 in FIG. 17.

In one embodiment, an infinite impulse response (IIR) filter is employed as an inverse filter in the signal separation/restoration module 76 for purposes of restoring the thermal signal content of a highpass filtered readback signal. The impulse response of an IIR filter is of infinite duration, in contrast to a FIR filter in which the impulse response has a finite duration. Unlike a FIR filter which may exhibit a perfect linear phase response, the phase response of an IIR filter is non-linear, especially at the band edges. Although an analog filter may be employed in an alternative embodiment, an IIR filter offers a number of advantages well-suited for use as an inverse filter for purposes of restoring the amplitude and phase of a thermal signal distorted by the highpass filtering behavior of the analog AE module 74.

Figure 18:
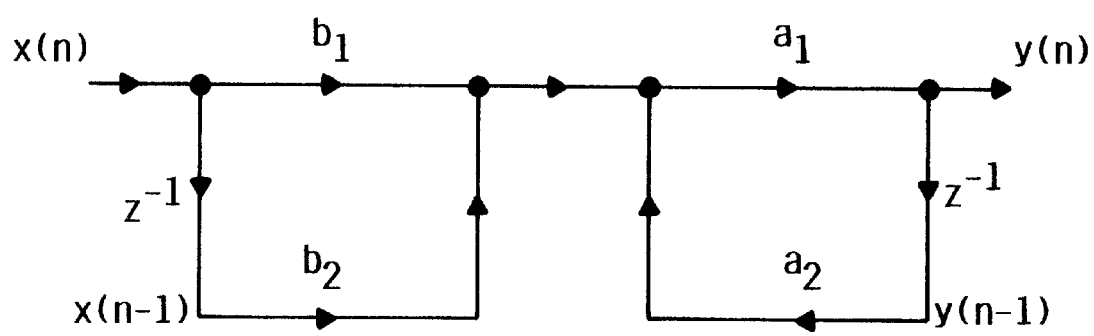
FIG. 18 is a signal flow diagram representative of the inverse filter of FIGS. 16 and 17.

The signal flow diagram illustrated in FIG. 18 is representative of a first order TTR filter configured as an inverse filter. The coefficients associated with the signal flow graph of FIG. 18 for a first order IIR inverse filter having a transfer function given by equation [2] above are:

$a_1 = 0.9876$ $a_2 = -0.9876$ $b_1 = 0.1$ $b_2 = -0.9752$

For more details on designing, implementing, and programming an IIR filter suitable for use as an inverse filter in the signal separation/restoration module 76, reference is made to E. C. Ifeachor, B. W. Jervis, "Digital Signal Processing" (Addison-Wesley Publishing Company, Inc. 1993).

Figure 19A:
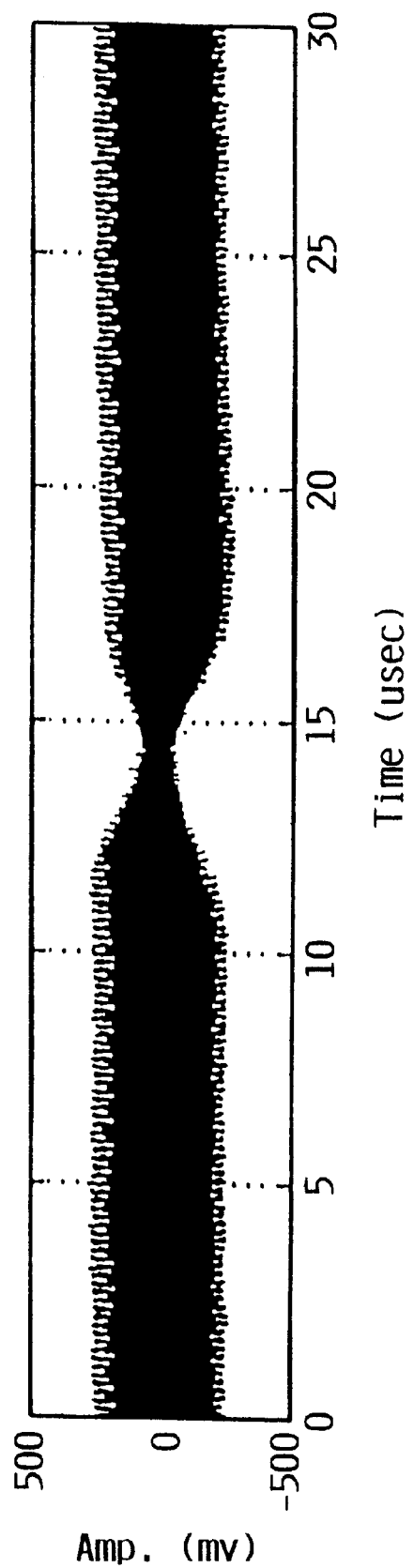
FIGS. 19($a$)–19($c$) show three waveforms caused by a disk surface pit produced at different processing points within a signal separation/restoration module.
Figure 19B:
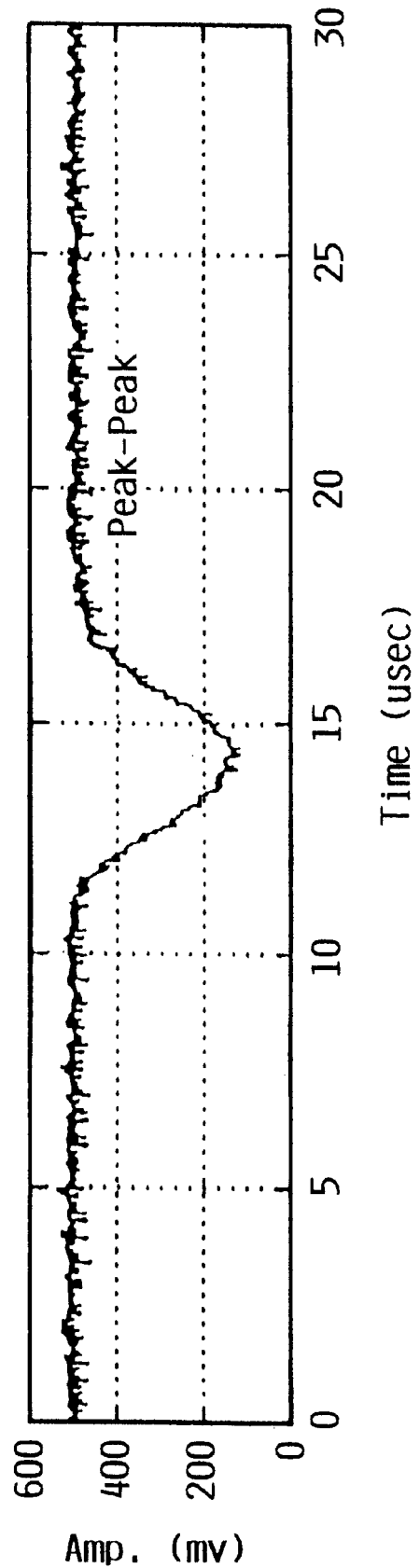
Figure 19C:
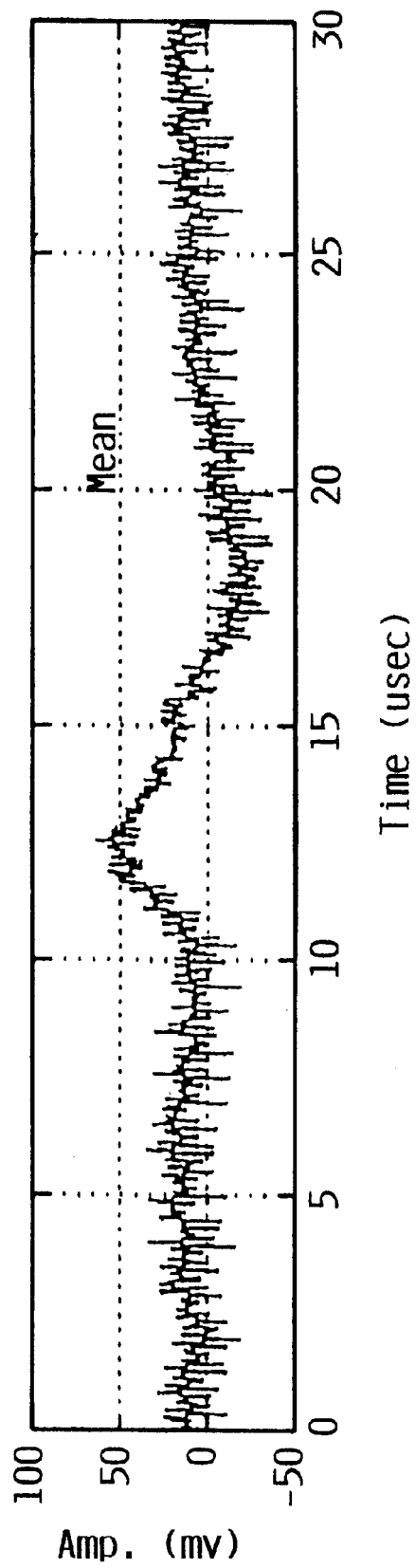

In FIG. 19, there is illustrated three waveforms that are used to demonstrate the effectiveness of an inverse filter for restoring the original amplitude and phase of the thermal signal component of a readback signal that has been passed through a highpass filter. In FIG. 19(a), there is shown a readback signal detected by scanning a pit in a data storage disk surface using an MR head. The magnetic readback signal shown in FIG. 19(a) was detected from a track written at a 20 MHz write frequency. The magnetic readback signal was sampled at 100 MHz with 8-bit resolution. The signal shown in FIG. 19(b) represents the calculated peak-to-peak magnitude of the readback signal of FIG. 19(a). Further, the signal shown in FIG. 19(b) represents the magnetic signal component of the readback signal shown in FIG. 19(a) which clearly demonstrates a significant reduction in amplitude due to the MR read element passing over the pit. FIG. 19(c) illustrates the thermal signal component of the readback signal of FIG. 19(a) after having been passed through the effective highpass filter of the AE module 74. It can be seen by comparing the waveforms of FIGS. 19(b) and 19(c) that the magnetic and thermal signal components of the readback signal do not correspond closely with one another. This poor correlation between the thermal and magnetic signals results from the distortion to the thermal signal caused by the effective highpass filtering nature of the analog AE module 74, which has effectively differentiated the thermal signal.

Figure 20:
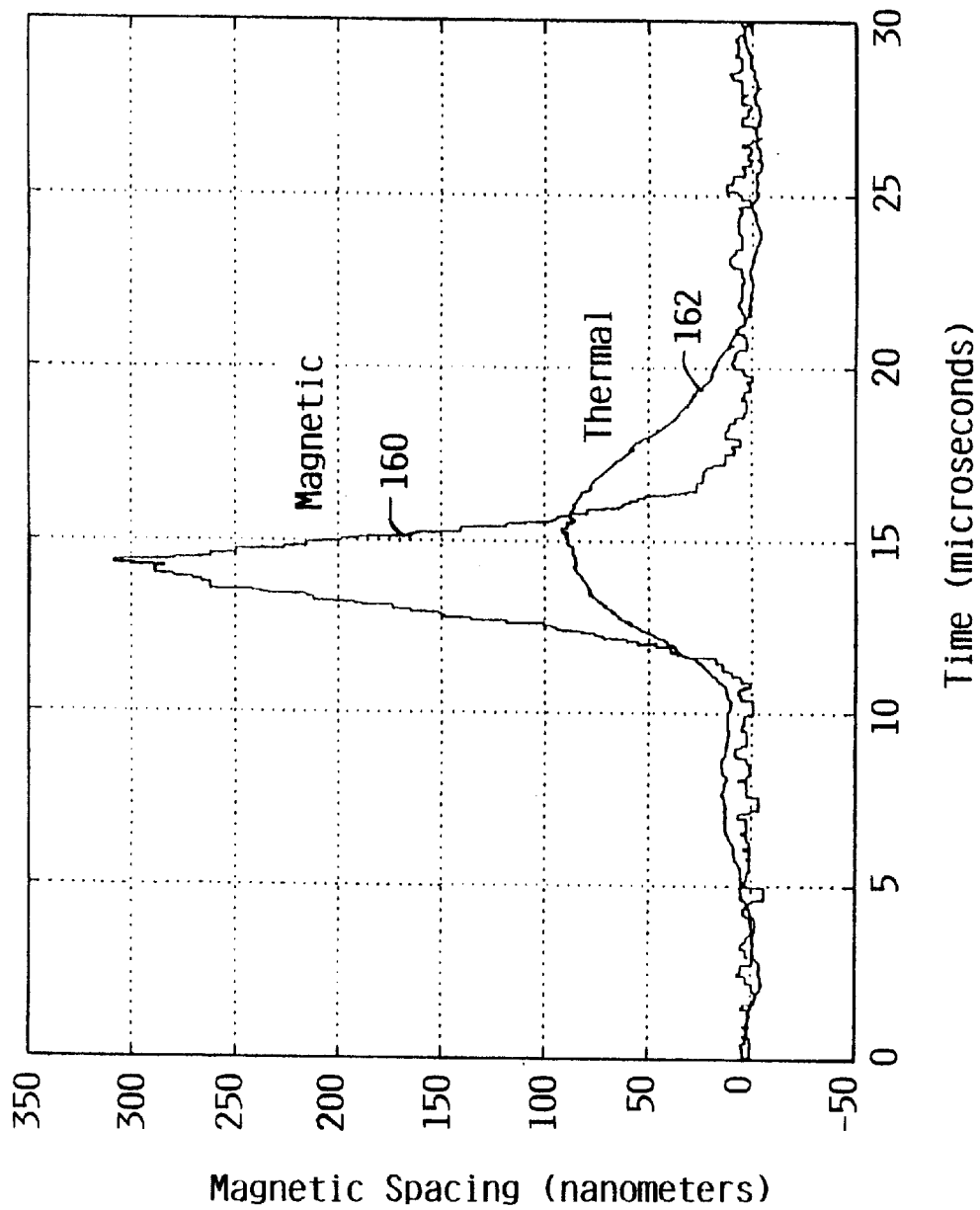
FIG. 20 is a showing of close correspondence between magnetic and thermal head-to-disk spacing signals associated with detection of a disk surface defect.

The inverse filter of the signal separation/restoration module 76 restores the amplitude and phase of the thermal signal 162 as illustrated in FIG. 20. It is noted that the thermal and magnetic signals illustrated in FIG. 20 are depicted as head-to-disk spacing signals, as will be discussed in detail hereinbelow. It can be seen that the magnetic signal and restored thermal signal demonstrate a close correspondence to one another after passing the highpass filtered thermal signal through the inverse filter.

The thermal signal induced in an MR head, as discussed previously with respect to FIG. 7, changes as a function of the head-to-disk spacing. The information contained in the thermal signal, therefore, can be used to detect variations in the surface topography of a disk. Various surface features, such as pits, gouges, bumps, thermal asperities, particulate contaminates, and the like, may be detected using the thermal signal. It is understood that such surface features may be purposefully incorporated into the disk surface for deriving various types of information using the thermal signal.

Concentric and radial elongated depressions, for example, may be included in the disk surface for purposes of determining track and sector locations using the thermal signal. Also, a detailed topographical mapping of the surface of a disk may be accomplished using the thermal signal. It can be appreciated that the availability of the thermal signal extracted from a readback signal can be advantageously exploited for use in a wide variety of applications. By way of further example, one or more depressions may be fabricated into the disk surface to a known depth for purposes of calibrating the thermal response of an MR head in order to derive head-to-disk spacing measurements using the thermal signal.

It is known by those skilled in the art to use a magnetic readback signal produced by a read/write transducer to determine spacing changes between the surface of a disk and the transducer. One such method for determining head-to-disk spacing using a magnetic readback signal is referred to as a Harmonic Ratio Flyheight (HRF) clearance test. The HRF test is a known method for measuring the flyheight of a slider supporting a transducer that is performed in-situ, or within the data storage system housing, using a magnetic head-to-disk spacing signal. The HRF method is described in U.S. Pat. No. 4,777,544, which is assigned to the assignee of the present invention and incorporated herein by reference. The HRF measurement method is a continuous, instantaneous measurement of the ratio of two spectral lines in the spectrum of a readback signal. Both of the instantaneous spectral line amplitudes relate to the same volume element of the recording medium directly underneath the MR transducer. The HRF measurement method provides for the determination of the instantaneous head clearance with respect to the disk surface using a magnetic readback signal.

Figure 21:
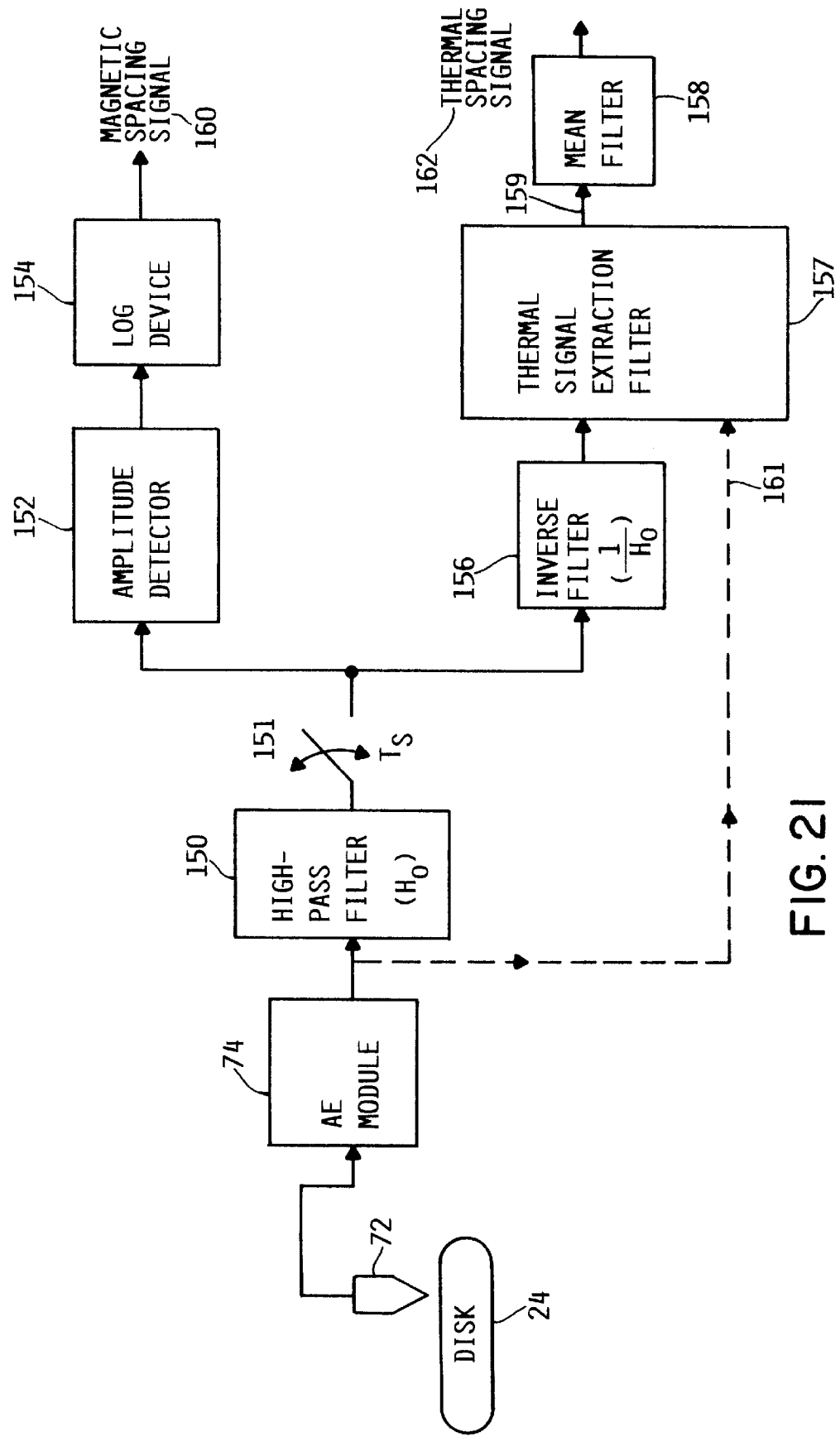
FIG. 21 is a block diagram of another embodiment of a signal separation/restoration module employing an infinite impulse response (IIR) filter.

In accordance with one embodiment, the thermal signal component of a readback signal induced in an MR head is used to qualitatively determine head-to-disk spacing change. In a further embodiment, the thermal signal is calibrated using the magnetic signal so as to provide for a quantitative determination of head-to-disk spacing. Referring to FIG. 21, there is shown in block diagram form a system for processing a readback signal to obtain magnetic and thermal head-to-disk spacing information. A readback signal is detected from the disk surface 24 by the MR element 72. It is assumed for purposes of illustration that the readback signal is a composite signal containing both magnetic and thermal signal components, it being understood that a readback signal devoid of a magnetic signal component contains a thermal signal component useful for determining head-to-disk clearance. The readback signal detected by the MR element 72 is communicated to the AE module 74 and then to a highpass filter 150. The highpass filter 150 is shown as a component external to the AE module 74, but is provided to generally represent the highpass filtering behavior of the AE module 74. The transfer function of the effective highpass filter 150 is denoted as $H_0$. The output signal from the highpass filter 150 is sampled by an analog-to-digital converter 151 to create digitized samples of the highpass filtered readback signal.

As illustrated in FIG. 21, the thermal signal, indicated at a point 159 at the output of the thermal signal extraction filter 157, may be produced using any of the methods discussed hereinabove. For example, the digitized readback signal may be communicated to an inverse filter 156 which corrects for the distortion introduced by the highpass filter 150 of the AE module 74. The transfer function of the inverse filter 156 is denoted as $H_0^{-1}$. The thermal signal is then extracted by the thermal signal extraction filter 157, which may be a FIR filter. It is understood that the inverse filter 156 and the thermal signal extraction filter 157 may be embodied in a signal IIR filter to restore the thermal signal distorted by the highpass filter 150. Alternatively, the readback signal may be tapped at a point prior to the highpass filter 150 and input to the thermal signal extraction filter 157, which may be a FIR filter as discussed in detail hereinabove. The thermal signal extracted by the thermal signal extraction filter 157 is communicated to a mean filter 158 which, in turn, produces a thermal spacing signal 162 that is linearly related to the head-to-disk spacing. The mean filter 158 is a digital moving smooth averaging filter.

The readback signal provided at the output of the analog-to-digital converter 151 may also be communicated to an amplitude detector 152, such as a FIR filter, that detects the peak-to-peak amplitude of the readback signal and extracts the magnetic signal component from the readback signal. The logarithm of the magnetic signal is obtained by passing the magnetic signal through the log device 154, which produces a magnetic signal that is linearly related to the head-to-disk spacing. Having extracted both the magnetic and thermal spacing signals 160 and 162, respectively, the thermal signal can be calibrated since the magnetic calibration is known and only depends on the recorded wavelength of the signal. It is important to note that both the negative (or the inverse) of the magnetic spacing signal 160 and the extracted thermal signal 162 are linearly proportional to the head-to-disk spacing (y).

In FIG. 20, the thermal spacing signal 162, processed by the thermal signal extraction filter 157 and mean filter 158, is illustrated together with the magnetic spacing signal 160, which was processed through the amplitude detector 152 and log device 154. It is noted that the linearized magnetic spacing signal 160 is typically calculated by taking the logarithm of the peak-to-peak signal and then multiplied by the known sensitivity of the output voltage change to magnetic spacing change in accordance with the well-known Wallace equation. It can be seen in FIG. 20 that, except for a difference in signal height and a slightly longer time constant associated with the thermal spacing signal 162, the magnetic spacing signal 160 and thermal spacing signal 162 describe a disk surface pit. The thermal spacing signal 162 can be calibrated using the linearized magnetic spacing signal 160 in order to accurately reflect true head-to-disk spacing, as is discussed in greater detail hereinbelow.

An important advantage of the present invention concerns the ability to detect head-to-disk spacing changes in-situ, or within the housing of the data storage system, using the thermal response of the MR element 72. In-situ head-to-disk spacing measurements using the thermal response of the MR element 72 is useful for purposes of disk manufacturing testing and screening, and for performing predictive failure analysis (PFA) during the service life of the data storage system in the field. The thermal spacing signal 162 can further be used to detect head contact with the surface of a data storage disk.

Figure 22:
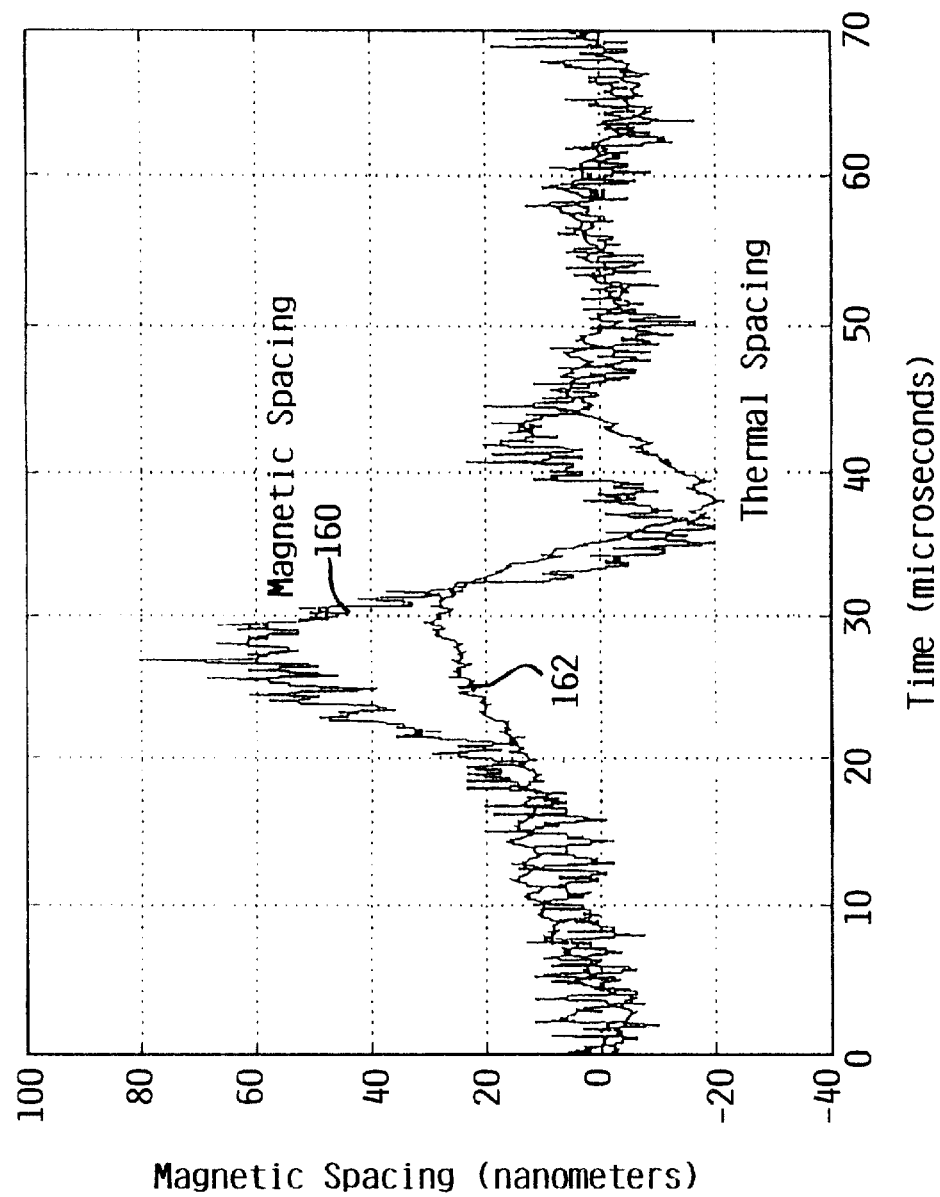
FIG. 22 is a showing of magnetic and thermal spacing signals associated with a head-to-disk contact event.

Referring now to FIG. 22, both the magnetic and thermal spacing signals 160 and 162 are shown for a head-to-disk contact event, such as contact between the MR head and a local thermal asperity (TA). The magnetic spacing signal 160 has been linearized by taking the logarithm of the magnetic signal. The thermal spacing signal 162 has been determined by using the inverse filtering approach previously described. It can be seen that there is an increase in the MR element-to-disk spacing as the disk asperity displaces the MR element 72 in an upward direction from the surface of the disk. Both the magnetic and thermal spacing signals 160 and 162 indicate this gradual increase in head-to-disk spacing between 0 to about 25 microseconds. After the MR element 72 passes over the asperity, there occurs some amount of air-bearing (head-to-disk spacing) modulation before the MR element 72 returns to its steady-state flying height. The air-bearing modulation can be seen in FIG. 27 beginning at approximately 35 microseconds and continuing through 70 microseconds.

The similarities in the waveform features for the magnetic and thermal spacing signals 160 and 162 demonstrate that the thermal spacing signal 162 can be used for detecting head-to-disk contact in-situ, without resorting to test bench equipment or external testers. It is noted that the characteristics of the inverse filter required for a particular data storage system will depend on the pole location for the highpass filter 150 of the AE module 74. For an embodiment employing an IIR filter or FIR filter, only the coefficients or tap weights need to be modified. In an embodiment employing the IIR filter, this modification can be made adaptively or dynamically in the event that there are variations in the pole frequency of the highpass filter 150. Such variations typically occur with changes in temperature, for example. It is to be understood that the inverse filter 150 described herein is not limited to first order IIR structures.

The magnitude of the thermal signal induced in an MR head is generally a function of the particular MR element used in the MR head. Variations in the manufacturing process and materials used, for example, will cause variation in the response of an MR element. Thus, in order to accurately determine head-to-disk spacing change using the thermal response of an MR head, it is desirable to calibrate the thermal response in-situ using the magnetic response. For example, accurate magnetic spacing information can be obtained using the well-known Wallace spacing loss equation. A calibration depression, such as a radial trench or pit, may be fabricated in the landing zone and used to produce both thermal and magnetic signal modulation for purposes of performing in-situ thermal spacing calibration. The magnetic spacing can be accurately determined for the trench which, in turn, can be used to calibrate the thermal voltage response of the MR element.

Another method involves combining a magnetic head-to-disk spacing measurement, obtained using the HRF method or other similar method, with a thermal clearance measurement. In accordance with this combined test, a simultaneous thermal and magnetic "spindown" is performed whereby the thermal voltage change between two disk velocities is compared to the known (HRF) spacing change between the two disk velocities. Recovery of the thermal signal at the disk rotation rate, however, may be difficult to achieve in a system employing an AE module 74 having a highpass filtering behavior since the highpass cutoff frequency is typically several orders of magnitude greater than the disk rotation frequency.

The head-to-disk spacing calibration of the thermal response of the MR head is made more complex by the highpass frequency filtering nature of the AE module 74. The transfer function $H_{AE}(s)$ of an AE module 74 having a highpass filtering behavior may be generally represented to a first order approximation as:

$$H_{AE}(s) = K_{AE} \frac{s}{s+a} \qquad [3]$$

where $K_{AE}$ is the gain of the AE module 74 at recording frequencies, and "a" is the cutoff frequency for the effective highpass filter incorporated into the AE module 74. A typical value of the gain is $K_{AE}$=170, but the gain of the AE module 74 generally has a large variance. The typical cutoff frequency "a" is approximately 325 KHz, and generally has associated with it a large tolerance of +/−125 KHz.

The frequencies of interest for bump-like surface defects to be detected during a surface analysis screening typically range between 10 KHz and 100 KHz. The thermal response of the MR head will translate these frequencies directly, while the magnetic response will shift these frequencies up in the 20 MHz range due to the magnetic recording carrier frequency. The highpass nature of the AE module 74 will attenuate all bump disturbance amplitudes in the thermal response for frequencies below 400 KHz by various amounts, while the magnetic response will be unaffected. In order to restore the attenuation of the thermal response, some form of integration must be applied. This restoration process can be accomplished by employing an inverse filter having a transfer function $H_{INV}(s)$ that is inverse to the transfer function $H_{AE}(s)$ of the AE module 74 (i.e., $H_{INV}(S)=1/H_{AE}(s)$). The lowest frequency present from an MR head reading data from a disk spinning at 7200 RPM, for example, is 120 Hz, and the lowest frequency for detecting disk surface bumps is approximately 10 KHz. As such, a pseudo-inverse filter, such as a lead-lag filter with a zero ("a") at 400 KHz and a pole ("b") at 5 KHz, may be more appropriate for this application.

The pseudo-inverse filter would have a transfer function of the form:

$$H_{P\_INV}(s) = \frac{s+a}{s+b} \quad [4]$$

and the overall transfer function of the pseudo-inverse filter cascaded with the AE module 74 becomes:

$$H(s) = H_{AE}(s)H_{P\_INV}(s) = K_{AE}\left(\frac{s}{s+a}\right)\left(\frac{s+a}{s+b}\right) = K_{AE}\frac{s}{s+b} \quad [5]$$

Thus, the compensated transfer function H(s) above will be a highpass filter with a cutoff frequency at 5 KHz, which is adequate to pass the frequencies associated with disk surface bumps in a non-distorted form.

The large variation in the highpass cutoff frequency "a" can cause large variations in the restored thermal response. An accurate estimation of the highpass cutoff frequency "a", the gain $K_{AE}$, and the sensitivity [nm/mv] for each MR head is important for reliable calibration. Due to the lack of a low frequency (i.e., ≦120 Hz) response of the AE module 74, the thermal calibration process may be supported by another method as a standard of reference. This supportive method is referred to herein as the magnetic Readback Signal Modulation (RSM) method, which is a known self-calibrating method for determining changes in head-to-disk magnetic spacing based on the Wallace spacing loss approach. An effective thermal calibration procedure is partially based on the RSM method and performed initially while the actuator is held against the crash stop in the landing zone to examine both the thermal and magnetic components of a readback signal of a track containing the calibration depression.

The calibration depression is fabricated on both surfaces of a disk blank and is subjected to polish and sputtering processes to permit both magnetic and thermal data to be obtained from the fabricated depression. It is noted that the depression fabricated in the landing zone could alternatively be fabricated as a manufactured bump. A bump, however, is more likely to cause head/disk interference (HDI) and may cause permanent damage to the head or the disk as a result of a head-to-disk crash. A bump may also cause head lift-off and air-bearing modulation and is therefore likely unsuitable for use as a permanent calibration site. A "pure" pit, in contrast, does not cause head lift-off nor any air-bearing modulation. The calibration trench on a disk substrate surface is also inexpensive to manufacture.

Prior to discussing one embodiment of a calibration procedure, it may be helpful to define several variables that are associated with the calibration process. It is noted that the term LF (Low Frequency) refers to frequencies on the order of disk rotation frequencies (RPM/60), such as 120 Hz at a rotation rate of 7200 RPM. Referring to equations 6 and 7, the term $v_{TH}(LF)$ represents the per revolution average of the AE module restored thermal voltage (baseline) response in the landing zone excluding the data obtained from the calibration pit, and is typically represented in millivolts (mv). The term $v_{TH}(Pit)$ is the AE module restored average thermal voltage peak produced from a calibration pit in the landing zone taken over several revolutions, and is typically represented in millivolts (mv). The term $\delta_{HRF}(LF)$ represents the per revolution average estimate of the RSM head-to-disk separation distance in the landing zone excluding the data obtained from the calibration pit, and is typically represented in nanometers (nm). Finally, the term $\delta_{HRF}(Pit)$ is the average peak HRF head/disk spacing produced from a calibration pit in the landing zone taken over several revolutions, and is typically represented in nanometers (nm).

The proposed thermal calibration process is predicated on using the per revolution average, low frequency (LF) RSM estimate of the head-to-disk spacing $\delta_{HRF}(LF)$, and the corresponding average thermal baseline voltage $v_{TH}(LF)$ obtained jointly with the actuator leaning up against the crash stop in the landing zone and excluding the data obtained from the calibration pit. The average peak value of the excluded thermal and magnetic pit data will yield $v_{TH}(Pit)$ and $\delta_{HRF}(Pit)$.

The "AC" calibration coefficient C(i) for the ith head can now be determined from:

$$C(i) = \frac{\delta_{HRF}(LF) - \delta_{HRF}(Pit)}{v_{TH}(Pit) - v_{TH}(LF)} \quad [nm/mv] \quad [6]$$

It should be observed that for a pit, the following conditions apply: $\delta_{HRF}(LF) > \delta_{HRF}(Pit)$ and $\delta_{TH}(LF) > \delta_{TH}(Pit)$. The approximate formula for the ith thermal head-to-disk spacing becomes:

$$\delta_{TH}(i) = \delta_{HRF}(LF) + C(i) \cdot \Delta v_{TH} \quad [7]$$

where $\Delta v_{TH} = v_{TH}(defect) - v_{TH}(LF)$. In the case of a bump, cooling is present, assuming there is no head-to-MR element contact, thus $\Delta v_{TH} < 0$. In the case of a pit, MR element heating will occur because of increased head-to-disk separation, thus $\Delta v_{TH} > 0$. Since the approximate thermal head-to-disk spacing formula was calibrated at the location of the calibration pit (i.e., the inner diameter landing zone in this case, but could be at the outer diameter for a load/unload disk drive), improved accuracy may be realized by updating the average RSM head-to-disk spacing $\delta_{HRF}(LF)$ at the track radius where the defect occurred. To accomplish this during manufacturing screening, a magnetic track would be written at the defect radius.

Even without calibration of the thermal response of the MR head, the thermal signal component of a readback signal can be used to provide a qualitative rather than a quantitative analysis of the disk surface characteristics. A disk surface analysis screening may, therefore, be performed to detect disk defects using an inherent normalization approach. One such approach is predicated on using the inherent "background" thermal signal information on a disk track as a reference from which clip levels (i.e., failure thresholds) are derived. It is important to note that both a quantitative and qualitative evaluation of the surface topography of a disk may be performed without a magnetic coating being applied to the disk surface. Thus, a disk blank which is devoid of a magnetic coating may be thoroughly analyzed for the presence of surface defects and features, whether purposefully or unintentionally provided thereon, prior to further processing the disk blank. As such, costly processing of a defective disk blank can be avoided.

The thermal background signal for a typical magnetic data storage disk may be viewed as being composed of five primary groups of frequencies. The first group includes servo pattern frequencies which are dominant and typically range between 2.5 MHz and 10 MHz. The second group includes servo-length frequencies defined from the beginning to the end of each servo burst typically ranging between 60 KHz and 70 KHz. The third group includes inter-servo frequencies, or the inverse of the time between servo bursts, at approximately 10 KHz. The fourth group of frequencies are the data pattern frequencies which exceed 10 MHz. The magnetic data pattern can be eliminated if a track is erased.

The fifth group of frequencies are broad band and relate to the disk topography, whereby the head-to-disk spacing changes as a result of surface variations of the disk. The upper end of the fifth group is limited by the thermal time constant of the MR response, which is typically about 1 microsecond. With proper filtering, the effect of readback signal amplitude modulation of these five "noise" sources can be selectively suppressed. It is noted that signal-to-noise ratios for head-to-disk contact events are typically in excess of 10:1 (20 db) and can be easily detected.

A number of filtering schemes may be employed to filter the five noise sources identified above. Such filtering schemes include the use of elliptic filters to filter the readback signal. Bandstop elliptic filters offer high attenuation and less phase distortion than either Butterworth or Chebyshev filters. One useful filtering scheme uses two elliptic bandstop filters. Each fourth order digital elliptic bandstop filter has two notches caused by two pairs of complex zeros in the transfer function that are located on the unit circle in the z-plane. One "low notch" fourth order elliptic filter would eliminate frequencies below approximately 15 KHz. In practice, the inter-servo pattern frequency is the most problematic as it is close to the desired detection bandwidth for disk surface defects. The low-notch elliptic filter can be designed to provide a notch at 120 Hz and 10.8 KHz which provides very high attenuation (e.g., 20–60 db) in this frequency range. A second fourth order elliptic notch filter configured as a high-notch filter would attenuate the servo pattern frequency of approximately 5 MHz and its third harmonic of approximately 15 MHz. These two frequencies are dominant. A fourth order elliptic notch filter can provide very high attenuation in this frequency range. These frequencies are stationary due to the precise velocity of the spindle of a typical data storage system.

As described above, both the magnetic and thermal components of the readback signal contain information about surface characteristics of the disk surface from with the readback signal was read. A comparison between the magnetic and thermal spacing signal response to various types of disk surface defects and permanently written servo sectors is provided below in Table 1. By separating a composite readback signal into independent magnetic and thermal signal components, there is provided an opportunity to use two independent, simultaneous responses of the MR head to detect the same "unknown phenomenon" or surface defect. Using the two independent thermal and magnetic signals during disk surface analysis provides for significantly increased defect detection resolution and reliability. Enhanced defect detection is realized by using a two dimensional (2D) detection approach rather an one dimensional (1D) approach. A one dimensional detection approach is referred to as an approach that employs either the magnetic or thermal signal, but not both. The use of the two independent magnetic and thermal signals obtained from same MR element at the same instant in time provides a powerful tool for detecting and classifying unknown disk surface defects.

A summary of differences between the magnetic and thermal MR head-to-disk spacing response to the simple disk surface defects and permanent recording shown in FIG. 7 is provided below in Table 1. It is to be understood that many disk surface defects, such as scratches and gouges, are typically complex combinations of several simple defects, and as such, will yield a more complex MR head response.

TABLE 1

| | Peak Response to Surface Defects and Servo Sectors | |
| --- | --- | --- |
| Type of Defect | Thermal Spacing Signal | Magnetic Spacing Signal |
| Pit | Positive | Positive |
| Bump | Negative | Positive |
| Thermal Asperity | Large Positive | Negative |
| Magnetic Void | None | Positive |
| Servo Sector | None | Negative and Positive |

Referring to the Table 1 above, a method for performing a disk surface defect analysis may be performed as follows. First, a thermal scan is performed on each surface of each disk provided in a data storage system. The resulting thermal response is monitored for thermal voltages exceeding predetermined positive and negative thresholds. Since the thermal response is insensitive to magnetic voids and pre-written servo sectors, this process will eliminate the magnetic patterns in servo sectors and magnetic voids as valid surface defects. It is noted that a defect analysis process exclusively utilizing a magnetic signal would erroneously indicate the presence of a surface defect upon detecting a magnetic void or misplaced permanent recording. Triggering of the thermal threshold detectors during the thermal scan can then be attributed to three basic types of surface defects, namely, pits, bumps, and thermal asperities (TAs), or combinations of these three defect types.

Magnetic information may then be written at the disk surface location at which a thermal threshold was triggered for purposes of performing a magnetic defect verification procedure, such as by use of the HRF or RSM methods, using the magnetic response characteristics provided in Table 1 above. Since only bumps and thermal asperities should indicate a valid failure condition, simultaneous triggering of both thermal detectors and HRF/RSM detectors must occur prior to rejecting the disk or the data storage system within which the defective disk is housed.

Thus, the heating and cooling of the MR element in response to head-to-disk spacing change can be used to detect and discriminate between mechanical damage to the disk 24, which should be sufficient cause to reject the disk, and other non-fatal disk defects such as pits and magnetic voids, which should not be sufficient cause to reject the disk. This disk surface defect analysis may be performed in-situ or within a fully operational data storage system prior to shipment. Additionally, the analysis may be performed in-situ during the in-field service life of a data storage system and at pre-established times for purposes of performing predictive failure analysis on the data storage system. Alternatively, the disk surface defect analysis may be performed on disk blanks devoid of a magnetic coating in order to avoid further processing of defective disk blanks.

A method for classifying disk defects can be formulated using the negative and positive peaks of the thermal signal extracted from an MR head. One embodiment of a defect classification method is derived from the determination that for disk depressions (e.g., pits), the thermal signal increases in amplitude as the MR element heats up due to the increased head-to-disk spacing. For this class of disk defects, there is seldom any cooling, which would result in the production of a negative polarity thermal signal by the MR head.

For conditions of near head-to-disk contact, the MR element cools. MR element cooling results in the production of a negative going thermal voltage signal $v_{TH}$. A criterion for testing a disk for mechanical damage is given by:

$$(V+) + |V-| > T \quad [8]$$

where, $V+$ is the positive peak of $v_{TH}$;

$V-$ is the negative peak of $v_{TH}$; and

T is the thermal voltage threshold which, if exceeded, indicates the presence of disk mechanical damage.

It has been determined by the inventors that the test criterion of equation [8] may be used to accurately identify the presence of existing or imminent mechanical disk damage. The application of equation [8] is appropriate for determining the presence of disk mechanical damage because such damage is associated with both heating, caused by the disk defect displacing a head, and cooling, caused by the MR element due to its proximity with the disk surface. For other disk defects not associated with upward disk surface protrusions, such as plating pits, the thermal voltage signal does not exhibit a sufficiently large negative peak to warrant concern, since there is no significant amount of MR element cooling that occurs. Moreover, disk defects which profoundly affect the magnetic signal, such as magnetic voids, do not result in the production of an appreciable thermal response. It has heretofore been common practice by the manufacturers of magnetic data storage disks to reject and discard suspect disks that exhibit non-catastrophic magnetic voids, since conventional screening procedures can not reliably verify the presence or absence of disk mechanical damage associated with the magnetic void or otherwise.

In general, a curve can be used to discriminate between a pass and fail screening criteria. An example of such a screening curve is given by the equation:

$$V_-^n + C_1 V_+^m = C_2 \quad [9]$$

where $V_-$ is the minimum thermal voltage, $V_+$ is the maximum thermal voltage, and n, m, $C_1$, and $C_2$ are constants. If n=m=2 and $C_1$=1, for example, then the pass-fail curve is a section of a circle with radius equal to $\sqrt{C_2}$.

Figure 23:
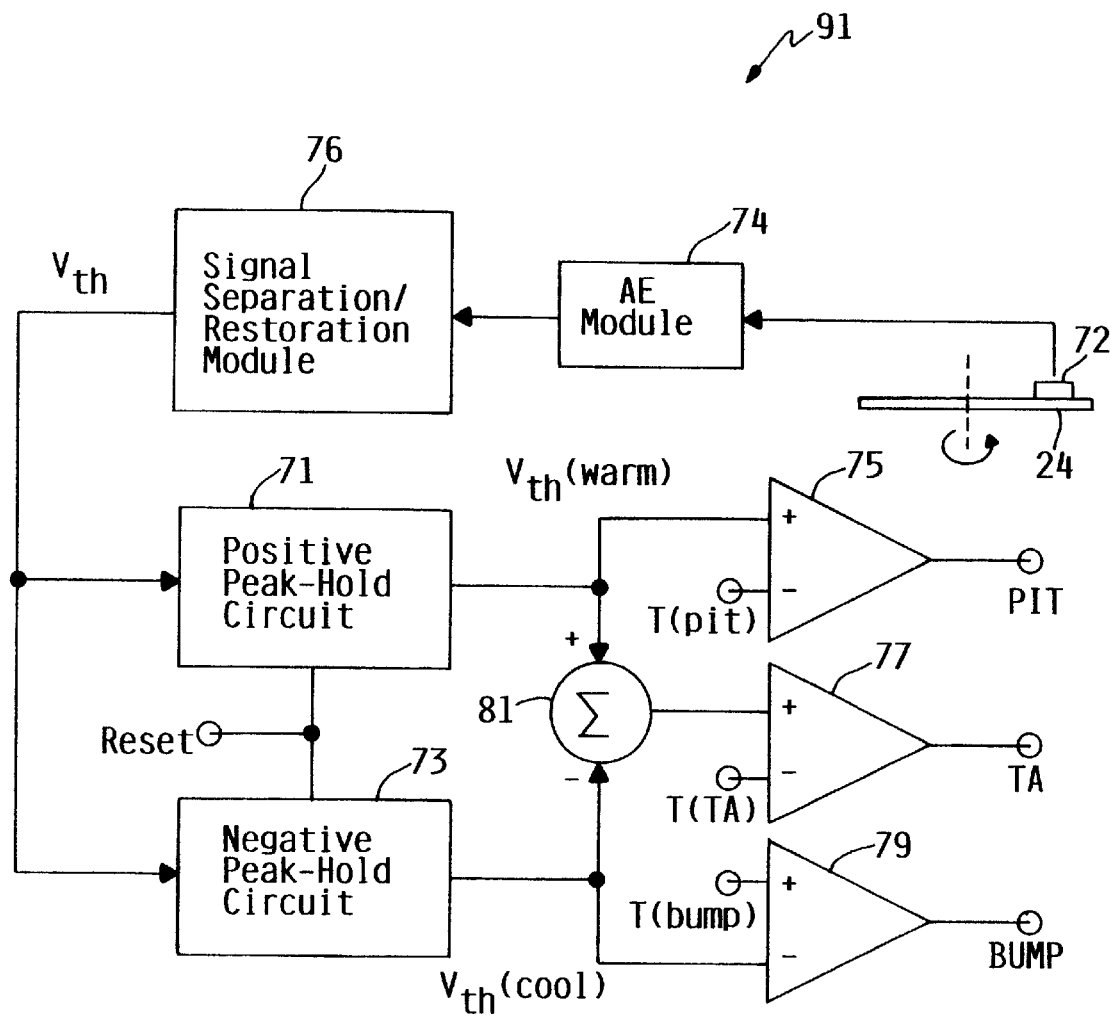
FIG. 23 is a block diagram of a defect classification circuit.

The identification of specific types of surface defects may be established by employing a disk surface defect detection circuit. In the embodiment illustrated in FIG. 23, a defect identification circuit 91 is implemented using an analog circuit, although it is understood that the defect identification circuit 91 may alternatively be implemented as a digital circuit or effectuated through digital signal processing. The defect detection identification 91 detects a thermal asperity (TA), for example, by measuring the total thermal voltage signal difference $\Delta v_{TH}$ (TA) between the negative thermal cooling peak $v_{TH}$ (cool) and the positive peak of the thermal asperity "heating" spike $v_{TH}$ (warm), as given by:

$$\Delta v_{TH}(TA) = V_{TH}(warm) - v_{TH}(cool) \quad [10]$$

A thermal voltage signal $v_{TH}$ is extracted from a readback signal by the signal separation/restoration module 76, and communicated to a positive peak-hold circuit 71 and a negative peak-hold circuit 73. The positive peak-hold circuit 71 buffers the positive peak voltage of the thermal signal $v_{TH}$ (warm), while the negative peak-hold circuit 73 buffers the negative peak voltage of the thermal signal $v_{TH}$ (cool). A pit detector 75, implemented using an operational amplifier in a comparator configuration, is calibrated to detect surface pits by comparing an appropriate input threshold voltage $T_{(PIT)}$ and the positive peak voltage $v_{TH}$ (warm).

A bump detector 79 is similarly implemented and calibrated to detect surface bumps by comparing an appropriate input threshold voltage $T_{(BUMP)}$ and the negative peak voltage $v_{TH}$ (cool). A thermal asperity detector 77 is also similarly implemented and calibrated to detect thermal asperities by comparing an appropriate input threshold voltage $T_{(TA)}$ and the thermal difference signal ($v_{TH}$ (warm) $- v_{TH}$ (cool)) produced by a summing circuit 81. In an embodiment that does not employ the positive and negative peak-hold circuits 71 and 73, the maximum positive and minimum negative peak values of the thermal response voltage $v_{TH}$ may be monitored continuously with respect to preset threshold values for defect identification.

The logic level of the three comparators 75, 77, and 79 may be configured to form a three bit word {TA, BUMP, PIT} used in connection with a pass/fail decision table as shown below in Table 2. As discussed previously, a verification procedure may be subsequently performed in the case of a disk failure by writing a magnetic track to the disk and performing an HRF and/or RSM verification test.

TABLE 2

| Comparator Logic Levels | | | |
|---|---|---|---|
| TA | BUMP | PIT | Pass/Fail Criteria |
| 0 | 0 | 0 | Pass |
| 0 | 0 | 1 | Pass |
| 0 | 1 | 0 | Fail (bump) |
| 0 | 1 | 1 | Fail (gouge) |
| 1 | 0 | 0 | Fail (TA) |
| 1 | 0 | 1 | Fail (TA) |
| 1 | 1 | 0 | Fail (large bump) |
| 1 | 1 | 1 | Fail (bump with TA) |

Figure 24A:
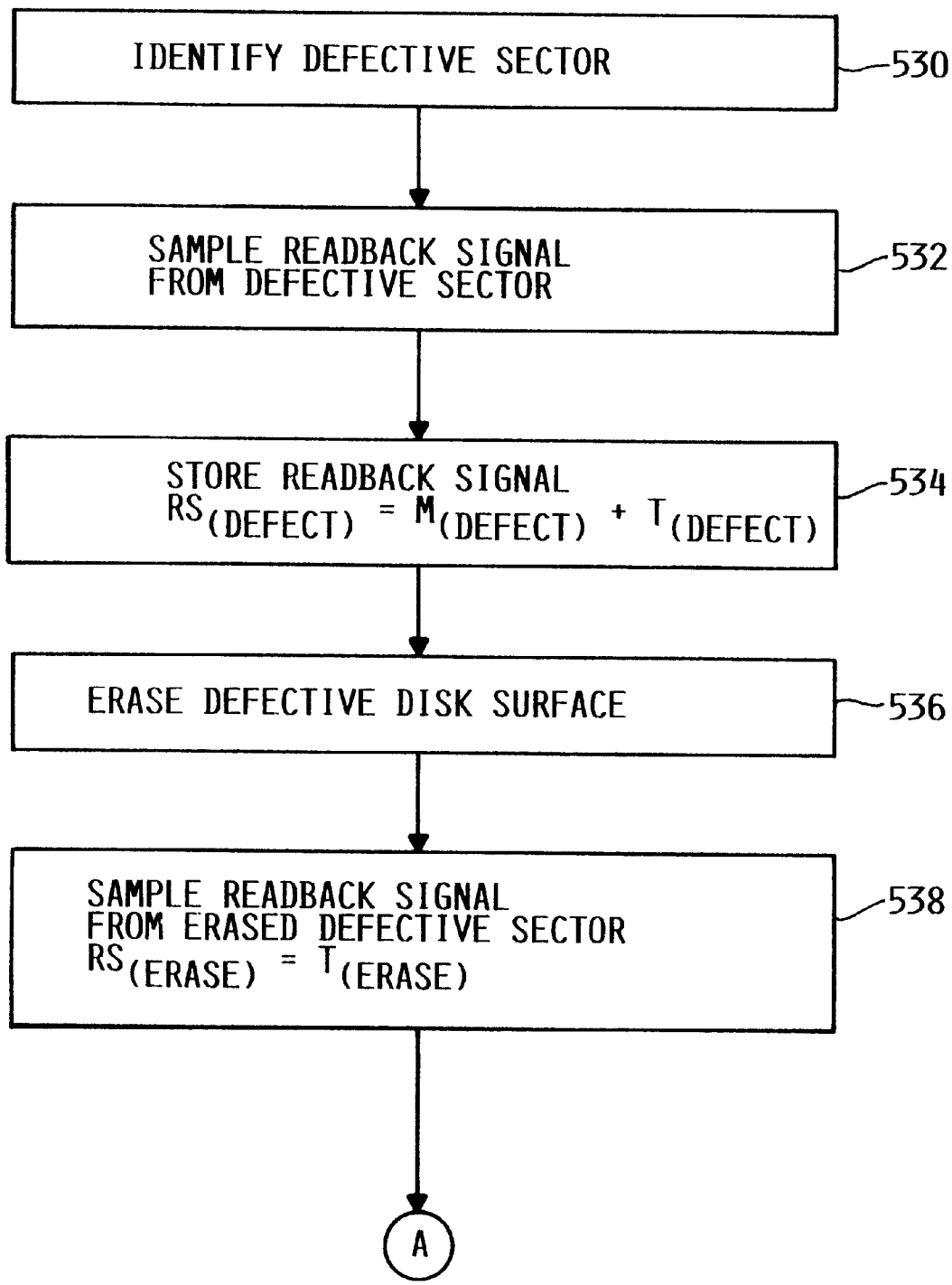
FIG. 24 is a flow diagram of an error recovery process using the thermal signal of a readback signal.
Figure 24B:
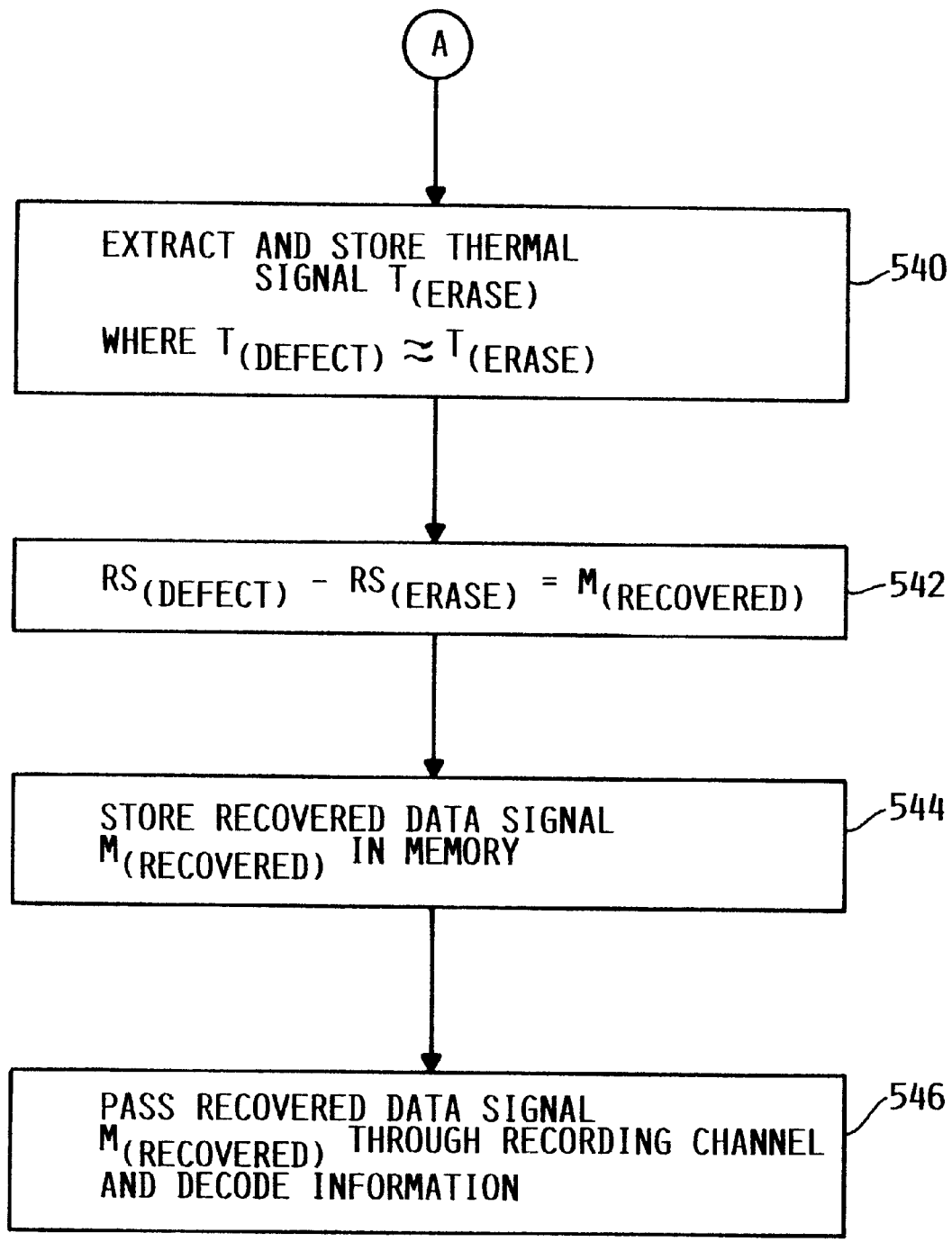

Referring to FIG. 24, there is illustrated various steps for performing an error recovery routine that utilizes a thermal signal component of a readback signal. The error recovery routine described in flow diagram form in FIG. 24 is generally appropriate for purposes of recovering data due to a severe error condition, and typically after performing a number of standard error recovery routines. At step 530, the defective sector containing lost or unreadable information is identified. A readback signal is sampled for the defective sector or disk area at step 532. The sampled readback signal is stored at step 534. The stored readback signal corresponding to a defective sector is indicated as $RS_{(DEFECT)} = M_{(DEFECT)} + T_{(DEFECT)}$, where $RS_{(DEFECT)}$ represents the total readback signal obtained from the defective sector, $M_{(DEFECT)}$ represents the magnetic signal component of the readback signal obtained from the defective sector, and $T_{(DEFECT)}$ represents the thermal signal component of the readback signal $RS_{(DEFECT)}$ obtained from the defective sector.

At step 536, the defective sector of disk surface area is erased. After completing erasure of the defective disk surface locations, a readback signal is sampled for the erased defective sector as indicated at step 538. The readback signal sample from the erased defective sector is represented as $RS_{(ERASE)} = T_{(ERASE)}$, where $RS_{(ERASE)}$ represents the total readback signal sampled from the erased defective sector, and $T_{(ERASE)}$ represents the thermal signal component of the readback signal $RS_{(ERASE)}$ obtained from the erased defective sector. It is noted that the magnetic signal component of the readback signal $RS_{(ERASE)}$ is not included since the erasure process eliminates substantially all of the magnetic signal component from the defective sector.

It is noted, however, that micro-fissures on the disk surface can maintain a small amount of magnetic flux, notwithstanding the erasure procedure. As such, it may be desirable to extract and store the thermal signal $T_{(ERASE)}$ from the readback signal derived from the erased defective sector, as indicated as step 540. It is noted that $T_{(DEFECT)}$ is substantially equivalent to $T_{(ERASE)}$ as verified by the thermal signal waveforms discussed hereinabove with respect to FIGS. 6(a) and 6(b). At step 542, the readback signal obtained for the erased defective sector at step 538 is subtracted from the readback signal derived from the defective sector at step 532. This subtraction produces the recovered magnetic signal component $M_{(RECOVERED)}$ of the defective sector, as indicated at step 542. The recovered magnetic signal $M_{(RECOVERED)}$ is then stored in memory or elsewhere on the data storage disk. In the last step 546, the recovered magnetic signal $M_{(RECOVERED)}$ is then passed from memory through the regular data recording channel where the information is decoded into binary words.

It will, of course, be understood that various modifications and additions can be made to the embodiments discussed hereinabove without departing from the scope or spirit of the present invention. Accordingly, the scope of the present invention should not be limited to the particular embodiments discussed above, but should be defined only by the full and fair scope of the claims set forth below.

What is claimed is:

1. A method for processing a signal obtained from a storage medium using a magnetoresistive (MR) element in proximity with the storage medium, the method comprising the steps of:

reading the signal from the storage medium using the MR element;

filtering the signal to produce a thermal signal component, the thermal signal component representing a thermal response of the MR element; and outputting the thermal signal component.

2. The method of claim 1, wherein the thermal signal component represents a distance between the MR element and the storage medium.

3. The method of claim 2, wherein the thermal signal component varies linearly in response to variations in the distance between the MR element and the storage medium.

4. The method of claim 1, wherein:

the signal comprises a magnetic signal component; and the thermal signal component is calibrated using the magnetic signal component such that the thermal signal component is used to estimate variations in spacing between the MR element and the storage medium.

5. The method of claim 1, wherein the signal comprises a magnetic signal component, and the method includes the step of:

producing a thermal spacing signal using the thermal signal component and the magnetic signal component, the thermal spacing signal varying proportionally to variations in spacing between the MR element and the storage medium.

6. The method of claim 5, wherein the thermal spacing signal varies linearly to the variations in spacing between the MR element and the storage medium.

7. The method of claim 1, wherein the thermal signal component represents a characteristic of the storage medium.

8. The method of claim 7, wherein the characteristic of the storage medium is a surface profile of the storage medium.

9. The method of claim 7, wherein the characteristic of the storage medium is an emissivity of the storage medium.

10. The method of claim 1, including the further step of filtering the signal to degrade the thermal component of the signal prior to filtering the signal to produce the thermal signal component.

11. The method of claim 1, wherein filtering the signal to produce the thermal signal component includes the step of filtering the signal using a finite impulse response (FIR) filter.

12. The method of claim 11, wherein the filtering step includes the step of programming the FIR filter using a set of tap weights stored in a memory coupled to the FIR filter.

13. The method of claim 12, wherein the filtering step includes the step of applying a window function to the set of tap weights when programming the FIR filter.

14. The method of claim 12, wherein the filtering step includes the steps of:

programming the FIR filter using a first set of tap weights for reading data stored on the storage medium; and programming the FIR filter using a second set of tap weights for reading servo information stored on the storage medium.

15. The method of claim 1, wherein the signal comprises servo information, and the extracted thermal signal component represents the servo information.

16. The method of claim 1, wherein the signal comprises a magnetic signal component representing servo information.

17. The method of claim 1, including the further step of producing a magnetic component using the signal.

18. The method of claim 1, wherein the signal comprises the thermal signal component and a magnetic signal component, the method including the further step of:

extracting the magnetic signal component from the signal by subtracting the extracted thermal signal component from the signal.

19. The method of claim 1, including the further steps of:

reading the signal from a defective portion of the storage medium, the signal being a composite signal comprising a magnetic signal component and the thermal signal component;

erasing the magnetic signal component from the defective portion of the storage medium;

extracting the thermal signal component from the erased defective portion of the storage medium; and subtracting the extracted thermal signal component from the composite signal to produce a restored magnetic signal substantially representative of the magnetic signal component of the composite signal.

20. A signal separating apparatus for an information storage device including an information storage medium, comprising:

a transducer including a magnetoresistive (MR) element;

a read channel connected to the transducer to read a signal from the storage medium with the MR element in proximity with the storage medium; and a filter, coupled to the read channel, that filters the signal to extract a thermal signal component of the signal, the thermal signal component, representative of a thermal response of the MR element, provided at an output of the filter.

21. The apparatus of claim 20, wherein the filter comprises a finite impulse response (FIR) filter.

22. The apparatus of claim 20, wherein the signal read from the storage medium comprises a magnetic signal component.

23. The apparatus of claim 20, wherein the signal read from the storage medium is a magnetic signal comprising the thermal signal component.

24. The apparatus of claim 20, wherein the signal read from the storage medium is a servo information signal.

25. The apparatus of claim 20, wherein the extracted thermal signal component is a servo information signal.

26. The apparatus of claim 20, comprising a magnetic signal filter coupled to the read channel for extracting a magnetic signal component of the signal read from the storage medium.

27. The apparatus of claim 20, comprising a signal summing device coupled to the read channel and the filter, wherein:

the signal summing device receives the extracted thermal signal component and a composite signal read from the storage medium comprising the thermal signal component and a magnetic signal component, and subtracts the thermal signal component from the composite signal using the extracted signal component to produce a restored magnetic signal substantially representative of the magnetic signal component of the composite signal.

28. An information storage device, comprising:

a transducer including a magnetoresistive (MR) element;

a storage medium;

means for moving at least one of the transducer and the medium to provide a relative movement between the transducer and the medium, the transducer being arranged relative to the medium such that a gap separates the MR element from the medium;

a read channel connected to the transducer to read a signal from the medium using the MR element; and a filter, coupled to the read channel, that filters the signal to extract a thermal signal component of the signal, the thermal signal component, representative of a thermal response of the MR element, provided at an output of the filter.

29. The device of claim 28, wherein the filter comprises a finite impulse response (FIR) filter.

30. The device of claim 29, comprising a memory coupled to the FIR filter, the FIR filter being programmable using a set of tap weights stored in the memory.

31. The device of claim 29, wherein:

the memory stores a set of window parameters; and the FIR filter is programmed using the set of tap weights and window parameters stored in the memory.

32. The device of claim 29, wherein:

a first set of tap weights is transferred from the memory to the FIR filter when the MR element moves in proximity with a data storing portion of the medium; and a second set of tap weights is transferred from the memory to the FIR filter when the MR element moves in proximity with a servo information storing portion of the medium.

33. The device of claim 28, wherein the signal read from the medium comprises a magnetic signal component.

34. The device of claim 28, wherein the signal read from the medium is a magnetic signal comprising the thermal signal component.

35. The device of claim 28, wherein the signal read from the medium is a servo information signal.

36. The device of claim 28, wherein the extracted thermal signal component is a servo information signal.

37. The device of claim 28, comprising a magnetic signal filter coupled to the read channel that produces a magnetic signal component of the signal read from the medium.

38. The device of claim 28, comprising a signal summing device coupled to the read channel and the filter, wherein:

the signal summing device receives the extracted thermal signal component and a composite signal read from the medium comprising the thermal signal component and a magnetic signal component, and subtracts the thermal signal component from the composite signal using the extracted signal component to produce a restored magnetic signal substantially representative of the magnetic signal component of the composite signal.

39. The device of claim 28, comprising a signal summing device and a write element, wherein:

the MR element reads the signal from a defective portion of the storage medium, the signal being a composite signal comprising a magnetic signal component and the thermal signal component;

the write element erases the magnetic signal component from the defective portion of the storage medium;

the filter extracts the thermal signal component from the erased defective portion of the storage medium; and the signal summing device subtracts the extracted thermal signal component from the composite signal to produce a restored magnetic signal.

40. The device of claim 39, wherein the restored magnetic signal is decoded in the read channel.

41. A method of examining a medium using a signal induced in a magnetoresistive (MR) element spaced apart from the medium, comprising the steps of:

reading the signal using the MR element as the MR element moves relative to the medium;

detecting a variation in a thermal signal component of the signal read by the MR element; and determining a change in a characteristic of the medium from the variation in the thermal signal component.

42. The method of claim 41, wherein the change in the characteristic of the medium is a change in a surface profile of the medium.

43. The method of claim 41, wherein the change in the characteristic of the medium is a change in emissivity of the medium.

44. The method of claim 41, wherein the detecting step includes the step of detecting a change in spacing between the MR element and the medium.

45. The method of claim 44, including the steps of:

determining the spacing at a plurality of locations on a portion of the medium;

mapping a topographic representation of the portion of the medium using the spacing determined at the plurality of locations.

46. The method of claim 44, including the steps of:

detecting the variation in the thermal signal component at a plurality of locations on a portion of the medium; and mapping a representation of the portion of the medium using the variation in the thermal signal component at the plurality of locations.

47. The method of claim 44, wherein the characteristic of the medium is a surface profile of the medium, the method including the step of producing a thermal spacing signal from the thermal signal component, wherein the thermal spacing signal represents a measure of the spacing between the MR element and the surface of the medium.

48. The method of claim 44, wherein the characteristic of the medium is a surface profile of the medium, the method including the steps of:

detecting a variation in a magnetic signal component of the signal read from the medium using the MR element;

producing a magnetic spacing signal from the magnetic signal component, the magnetic spacing signal representing a measure of the spacing between the MR element and the surface of the medium; and producing a thermal spacing signal from the thermal signal component, the thermal spacing signal calibrated using the magnetic spacing signal so as to represent the measure of the spacing between the MR element and the surface of the medium.

49. The method of claim 44, wherein the characteristic of the medium is a surface profile of the medium, the method including the steps of:

determining a frequency of the thermal signal component; and associating the thermal signal component frequency to a surface profile feature of the medium.

50. The method of claim 44, the method including the step of detecting a variation in a magnetic signal component of the signal read from the medium using the MR element, wherein:

the characteristic of the medium is a surface profile of the medium; and the determining step includes the step of determining the change in the surface profile of the medium using the thermal signal component variation and the magnetic signal component variation.

51. The method of claim 44, wherein the characteristic of the medium is a surface profile of the medium, the method including the step of detecting a feature in the surface profile using the variation in the thermal signal component.

52. The method of claim 51, including the steps of:

writing a magnetic signal at a location on the medium corresponding to a location of the feature;

reading the magnetic signal using the MR element; and detecting the feature in the surface profile using the magnetic signal read using the MR element.

53. The method of claim 41, wherein the characteristic of the medium is a surface profile of the medium comprising depressions provided on a surface of the medium, and the method includes the step of:

detecting the depressions provided on the surface of the medium using the variation in the thermal signal component.

54. The method of claim 53, wherein the depressions comprise grooves provided on the surface of the medium.

55. The method of claim 53, wherein the depressions comprise pits provided on the surface of the medium.

56. An information storage device, comprising:

a transducer including a magnetoresistive (MR) element;

a storage medium;

means for moving at least one of the transducer and the medium to provide a relative movement between the transducer and the medium, the transducer being arranged relative to the medium such that a spacing separates the MR element from the medium;

a read channel connected to the transducer to read a signal from the medium using the MR element;

a filter, coupled to the read channel, for passing a thermal signal component of the signal, the thermal signal component representing a thermal response of the MR element; and a detector, coupled to the filter, for detecting a variation in the thermal signal component corresponding to a variation in a surface profile of the storage medium.

57. The device of claim 56, wherein the surface profile variation represents servo information.

58. The device of claim 56, wherein the thermal signal variation detected by the detector corresponds to a change in a dimension of the spacing between the MR element and the surface profile of the storage medium.

59. The device of claim 58, wherein the detector detects variations in the spacing dimension at a plurality of locations on a portion of the storage medium to characterize the surface profile variations of the portion of the storage medium.

60. The device of claim 56, wherein the detector detects variations in the thermal signal component at a plurality of locations on a portion of the storage medium to characterize the surface profile variations of the portion of the storage medium.

61. The device of claim 56, comprising a mean filter coupled to the filter for converting the thermal signal component to a thermal spacing signal, wherein the thermal spacing signal corresponds to a dimension of the spacing between the MR element and the surface of the medium.

62. The device of claim 56, comprising a magnetic signal filter coupled to the filter and a log filter for converting a magnetic signal component of the signal read from the storage medium using the MR element to a magnetic spacing signal, wherein the magnetic spacing signal corresponds to a dimension of the spacing between the MR element and the surface of the medium.

63. The device of claim 62, comprising a magnetic signal filter coupled to the filter and a log filter for converting a magnetic signal component of the signal read from the storage medium using the MR element to a magnetic spacing signal, wherein the magnetic spacing signal and the thermal spacing signal correspond substantially to the dimension of the spacing between the MR element and the surface of the medium.

64. The device of claim 56, comprising a defect characterization circuit for associating a frequency of the thermal signal component to a surface profile feature.

65. The device of claim 56, wherein:

the detector detects a variation in a magnetic signal component of the signal read from the storage medium using the MR element corresponding to a surface profile feature of the storage medium; and the detector detects the variation in the thermal signal component corresponding to the surface profile feature.

66. The device of claim 56, wherein the detector detects a surface profile feature of the storage medium as the variation in the thermal signal component.

67. A method of reading a signal from a medium using a single magnetoresistive (MR) element of a transducer, comprising the step of concurrently reading a first type of information and a second type of information included in the signal from the medium using the MR element, the first type of information being represented in a magnetic component of the signal and the second type of information being represented in a thermal component of the signal, the method further comprising filtering the signal and outputting the thermal component alone or together with the magnetic component.

68. The method of claim 67, wherein the first type of information comprises data and the second type of information comprises transducer location information.

69. A method for processing a signal obtained from a storage medium using a magnetoresistive (MR) element, the method comprising the steps of:

reading the signal from the storage medium using the MR element in proximity with the storage medium;

modifying the signal such that a thermal component of the signal representing a thermal response of the MR element is degraded; and altering the modified signal to produce a restored thermal signal substantially representative of the thermal component of the signal read from the storage medium.

70. The method of claim 69, wherein:

the signal read from the storage medium comprises a magnetic component and the thermal component;

the modifying step includes the step of filtering the signal so as to pass the magnetic component of the signal and to degrade the thermal component of the signal; and the altering step includes the step of filtering the modified signal to produce the restored thermal signal.

71. The method of claim 69, wherein the restored thermal signal represents a separation distance between the MR element and the storage medium.

72. The method of claim 71, wherein the restored thermal signal varies proportionally in response to variations in the separation distance between the MR element and the storage medium.

73. The method of claim 69, wherein the restored thermal signal represents a surface profile of the storage medium.

74. The method of claim 69, including the further step of producing a magnetic component using the signal.

75. A signal processing apparatus for an information storage device including an information storage medium, comprising:

a transducer including a magnetoresistive (MR) element in proximity with the storage medium;

a circuit, coupled to the transducer, for modifying a signal read from the storage medium using the MR element such that a thermal component of the signal representing a thermal response of the MR element is degraded; and a filter, coupled to the circuit, for producing a restored thermal signal substantially representative of the thermal component of the signal read from the storage medium using the modified signal received from the circuit.

76. The apparatus of claim 75, comprising a magnetic signal filter coupled to the circuit for passing a magnetic signal component of the signal read from the storage medium.

77. An information storage device, comprising:

a storage medium;

a transducer including a magnetoresistive (MR) element in proximity with the storage medium;

means for moving at least one of the transducer and the medium to provide a relative movement between the transducer and the medium;

a circuit, coupled to the transducer, for modifying a signal read from the storage medium using the MR element such that a thermal component of the signal representing a thermal response of the MR element is degraded; and a filter, coupled to the circuit, for producing a restored thermal signal substantially representative of the thermal component of the signal read from the storage medium using the modified signal received from the circuit.

* * * * *